(12) United States Patent
Ruiss et al.

(10) Patent No.: US 10,300,129 B2
(45) Date of Patent: May 28, 2019

(54) EPSTEIN-BARR-VIRUS VACCINE

(71) Applicant: HELMHOLTZ ZENTRUM MUNCHEN DEUTSCHES FORSCHUNGSZENTRUM FUR GESUNDHEIT UND UMWELT (GMBH), Neuherberg (DE)

(72) Inventors: Romana Ruiss, Munich (DE); Gilbert Reisbach, Munich (DE); Wolfgang Hammerschmidt, Munich (DE); Reinhard Zeidler, Olching (DE)

(73) Assignee: HELMHOLTZ ZENTRUM MUNCHEN DEUTSCHES FORSCHUNGSZENTRUM FUR GESUNDHEIT UND UMWELT (GMB), Neuherberg (DE)

( * ) Notice: Subject to any disclaimer, the term of this patent is extended or adjusted under 35 U.S.C. 154(b) by 81 days.

(21) Appl. No.: 15/077,477

(22) Filed: Mar. 22, 2016

(65) Prior Publication Data

US 2016/0296618 A1    Oct. 13, 2016

Related U.S. Application Data

(63) Continuation of application No. 13/818,711, filed as application No. PCT/EP2011/064672 on Aug. 25, 2011, now abandoned.

(60) Provisional application No. 61/377,027, filed on Aug. 25, 2010.

(30) Foreign Application Priority Data

Aug. 25, 2010    (EP) .................................. 10008835

(51) Int. Cl.
A61K 39/245    (2006.01)
C12N 7/00    (2006.01)
A61K 39/12    (2006.01)
C07K 14/005    (2006.01)
A61K 39/00    (2006.01)

(52) U.S. Cl.
CPC ............ *A61K 39/245* (2013.01); *A61K 39/12* (2013.01); *C07K 14/005* (2013.01); *C12N 7/00* (2013.01); *A61K 2039/5258* (2013.01); *A61K 2039/57* (2013.01); *A61K 2039/575* (2013.01); *C07K 2317/569* (2013.01); *C12N 2710/16223* (2013.01); *C12N 2710/16234* (2013.01); *C12N 2710/16252* (2013.01); *C12N 2710/16262* (2013.01); *C12N 2710/16271* (2013.01)

(58) Field of Classification Search
None
See application file for complete search history.

(56) References Cited

FOREIGN PATENT DOCUMENTS

WO    WO 2009068615    6/2009
WO    WO2009/068615    * 10/2009    ............ A61K 39/00

OTHER PUBLICATIONS

Romana Ruiss, (Induktion Epstein-Barr Virus-specifischer Immunantworten durch Exosomen and Virus-like Particles, Nov. 2009, p. 1-169.*
Yajima et al. (Journal of Infectious Diseases, 2009, vol. 200, p. 1611-1615).*
Becker, N et al., 2009. Medical history and risk of lymphoma: results of a European case-control study (EPILYMPH). J Cancer Res Clin Oncol 135, 1099-1107.
Braasch, D. A., et al., 2001. Locked nucleic acid (LNA): fine-tuning the recognition of DNA and RNA. Chem Biol 8, 1-7.
Bornkamm, G. W., et al., 2005. Stringent doxycycline-dependent control of gene activities using an episomal one-vector system. Nucleic Acids Res 33:e137.
Busse, C., et al., 2010. Epstein-Barr viruses that express a CD21 antibody provide evidence that gp350's functions extend beyond B-cell surface binding. J Virol 84, 1139-1147.
Calistri, A. et al., 2009. Role of multivesicular bodies and their components in the egress of enveloped RNA viruses. Rev Med Virol 19, 31-45.
Chesnokova, L. S. et al., 2009. Fusion of epithelial cells by Epstein-Barr virus proteins is triggered by binding of viral glycoproteins gHgL to integrins alphavbela6 or alphavbela8. Proc Nall Acad Sci U S A 106, 20464-20469.
Delecluse, H. J., et al., 1998. Propagation and recovery of intact, infectious Epstein-Barr virus from prokaryotic to human cells. Proc Nall Acad Sci U S A 95, 8245-8250.

(Continued)

*Primary Examiner* — Agnieszka Boesen
(74) *Attorney, Agent, or Firm* — Kagan Binder PLLC

(57) ABSTRACT

The present invention relates to a vaccine comprising a particle, said particle comprising (i) at least one Epstein-Barr virus (EBV) structural polypeptide, (ii) at least one EBV lytic polypeptide, (iii) membrane lipids, said particle being devoid of EBV DNA, wherein (a) the B-cell transformation capacity of one or more EBV polypeptides required for B-cell transformation as comprised in said particle is disabled while their immunogenicity is maintained; and or (b) said particle is devoid of one or more EBV polypeptides required for B-cell transformation. Furthermore, the invention relates to a method for generating a particle, to a cell obtained in the method of the invention, a kit comprising the vaccine or the particle generated according in the method of the invention. Also, the invention relates to the use of the vaccine or the particle generated according to the method of the invention for generating CD8+ cells specific for an EBV antigen.

9 Claims, 9 Drawing Sheets

Figure 1:
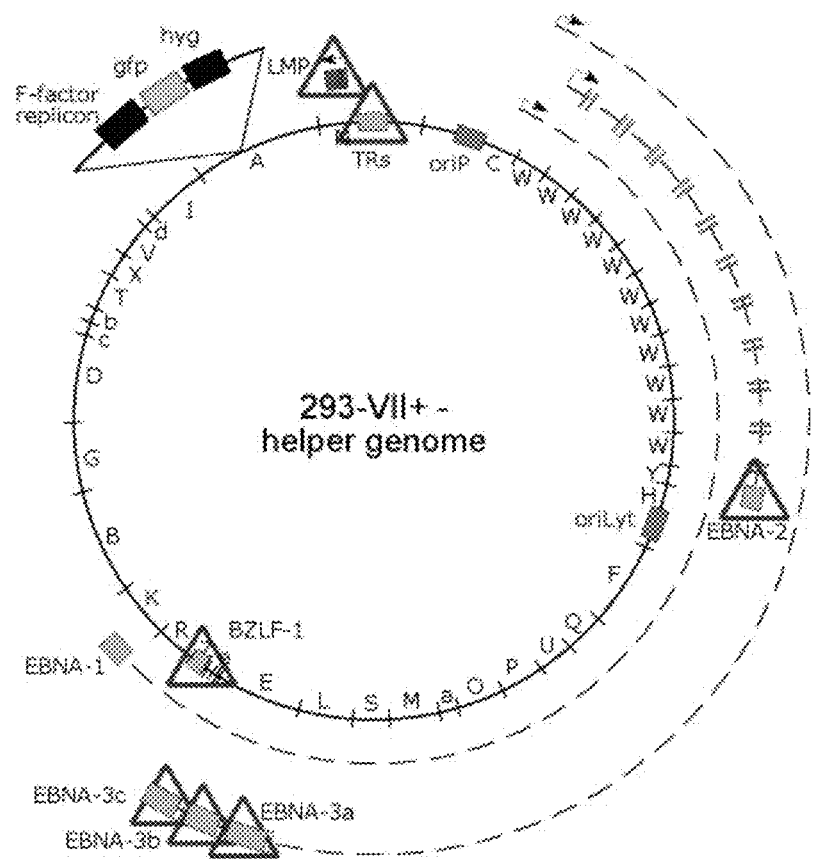

Specification includes a Sequence Listing.

(56) References Cited

OTHER PUBLICATIONS

Delecluse, H. J., et al., 1999. A first-generation packaging cell line for Epstein-Barr virus-derived vectors. Proc Nall Acad Sci U S A 96, 5188-5193.
Duchini, A., et al., 2003. Vaccinations for adult solid-organ transplant recipients: current recommendations and protocols. Clin Microbial Rev 16, 357-364.
Ellioll, S. L., et al., 2008. Phase I trial of a CD8+ T-cell peptide epitope-based vaccine for infectious mononucleosis. J Viral 82, 1448-1457.
Everly, M. J. et al., 2007. Posllransplant lymphoproliferative disorder. Ann Pharmacother 41, 1850-1858.
Forster, K., V. et al., 1999. Tetracycline-inducible expression systems with reduced basal activity in mammalian cells. Nucleic Acids Res 27:708-710.
Gires, 0., et al., 1997. Latent membrane protein 1 of Epstein-Barr virus mimics a constitutively active receptor molecule. EMBO J 16, 6131-6140.
Goldacre, M. J., et al., 2009. Associations between infectious mononucleosis and cancer: record-linkage studies. Epidemiol Infect 137, 672-680.
Green, K. J., et al., 2004. Potent T cell response to a class I-binding 13-mer viral epitope and the influence of HLA micropolymorphism in controlling epitope length. Eur J Immunol 34:2510-2519.
Gu, S. Y., et al., 1995. First EBV vaccine trial in humans using recombinant vaccinia virus expressing the major membrane antigen. Dev Biol Stand 84, 171-177.
Zalani, S., et al., 1996. Epstein-Barr viral latency is disrupted by the immediate-early BRLF1 protein through a cell-specific mechanism. Proc Nall Acad Sci U S A 93, 9194-9199.
Hislop, A. D., et al., 2007. Cellular responses to viral infection in humans: lessons from Epstein-Barr virus. Annu Rev Immunol 25, 587-617.
Imashuku, S. 2007. Systemic type Epstein-Barr virus-related lymphoproliferative diseases in children and young adults: challenges for pediatric hemato-oncologists and infectious disease specialists. Pediatr Hemalol Oneal 24, 563-568.
Janz, A., et al., 2000. Infectious Epstein-Barr virus lacking major glycoprotein BLLF1 (gp350/220) demonstrates the existence of additional viral ligands. J Virol 74, 10142-10152.
Johannsen, E., et al., 2004. Proteins of purified Epstein-Barr virus. Proc Nall Acad Sci U S A 101, 16286-16291.
Keller, S. A., et al., 2009. Follicular and marginal zone B cells fail to cross-present MHC class I-restricted epitopes derived from viral particles. J Immunol 182, 6261-6266.
Kempkes, B., et al., 1995. Immortalization of human B lymphocytes by a plasmid containing 71 kilobase pairs of Epstein-Barr virus DNA. J. Viral. 69:231-238.
Kieff, E., et al., 2007. Epstein-Barr Virus and Its Replication. In Fields Virology, Knipe, D., and P. Howley, eds. (Philadelphia, PA: Lippincott Williams & Wilkins), pp. 2604-2654.
Lopes, V., et al., 2003. Epstein-Barr virus-associated cancers: aetiology and treatment. Herpes 10, 78-82.
Lu, G., et al., 2009. Clinical analysis and follow-up study of chronic active Epstein-Barr virus infection in 53 pediatric cases. Chin Med J (Engl) 122, 262-266.
Mautner, J., et al., 2004. Epstein-Barr virus nuclear antigen 1 evades direct immune recognition by CD4+ T helper cells. Eur J Immunol 34:2500-2509.
Mendoza, F., et al., 2006. Post-transplant lymphoproliferative disorder following pediatric heart transplantation. Pediatr Transplant 10, 60-66.
Moosmann, A., et al., 2002. B cells immortalized by a mini-Epstein-Barr virus encoding a foreign antigen efficiently reactivate specific cytotoxic T cells. Blood 100:1755-1764.
Mori, Y., et al., 2008. Human herpesvirus-6 induces MVB formation, and virus egress occurs by an exosomal release pathway. Traffic 9, 1728-1742.
Moutschen, M., et al., 2007. Phase I/II studies to evaluate safety and immunogenicity of a recombinant gp350 Epstein- Barr virus vaccine in healthy adults. Vaccine 25, 4697-4705.
Niedobitek, G. 1999. The Epstein-Barr virus: a group 1 carcinogen? Virchows Arch 435, 79-86.
Omerovic, J. eta I., 2005. The amino terminus of Epstein-Barr virus glycoprotein gH is important for fusion with epithelial and B cells. J Viral 79, 12408-12415.
Pelchen-Matthews, A., et al., 2004. Endosomes, exosomes and Trojan viruses. Trends Microbiol 12, 310-316.
Pickering, L. K., et al., 2009. Immunization programs for infants, children, adolescents, and adults: clinical practice guidelines by the Infectious Diseases Society of America. Clin Infect Dis 49, 817-840.
Rees, L., et al., 2009. A phase I trial of epstein-barr virus gp350 vaccine for children with chronic kidney disease awaiting transplantation. Transplantation 88, 1025-1029.
Saulquin, X., et al., 2000. A global appraisal of immunodominant COB T cell responses to Epstein-Barr virus and cytomegalovirus by bulk screening. Eur J Immunol 30:2531-2539.
Silva, A. L., et al., 2004. Mutational analyses of Epstein-Barr virus glycoprotein 42 reveal functional domains not involved in receptor binding but required for membrane fusion. J Viral 78, 5946-5956.
Zaadslra, B. M., et al., 2008. Selective association of multiple sclerosis with infectious mononucleosis. Mull Seier 14, 307-313.
Sorem, J., and Longnecker, R. 2009. Cleavage of Epstein-Barr virus glycoprotein B is required for full function in cell- cell fusion with both epithelial and B cells. J Gen Viral 90, 591-595.
Succi, R. C., and Farhat, C. K. 2006. Vaccination in special situations. J Pediatr (Rio J) 82, S91-100.
Swerdlow, A. J., et al., 2000. Risk of lymphoid neoplasia after cardiothoracic transplantation. A cohort study of the relation to Epstein-Barr virus. Transplantation 69, 897-904.
Taylor, A. L., et al., 2005. Post-transplant lymphoproliferative disorders (PTLD) after solid organ transplantation. Crit Rev Oneal Hemalol 56, 155-167.
Thacker, E. L., et al., 2006. Infectious mononucleosis and risk for multiple sclerosis: a meta-analysis. Ann Neural 59, 499-503.
Tobi, M., et al., 1982. Prolonged atypical illness associated with serological evidence of persistent Epstein-Barr virus infection. Lancet 1,61-64.
Urlinger, S., et al., 2000. Exploring the sequence space for tetracycline-dependent transcriptional activators: novel mutations yield expanded range and sensitivity. Proc Natl Acad Sci U S A 97:7963-7968.
Sokal et al. "Recombinant gp350 vaccine for infectious mononucleosis: A phase 2, randomized, double-blind, placebo-controlled trial to evaluate the safety, immuongenicity, and efficacy of an Epstein-Barr virus vaccine in healthy young adults" Journal of Infectious Diseases, University of Chicago Press, vol. 196, No. 12, Dec. 15, 2007, pp. 1749-1753.
Morgan et al. "Chapter 72: Epstein-Barr virus vaccines" In: Arvin A, et al. "Human Herpesviruses: Biology, Therapy, and Immunoprophylaxis", 2007, Cambridge University Press.
Galarza et al. "Virus-Like Particle (VLP) Vaccine Conferred Complete Protection against a Lethal Influenza Virus Challenge." Viral Immunology, VOi. 18, No. 2, Jan. 1, 2005, pp. 244-251.
Feederle R. et al. "Defective infectious particles and rare packaged genomes produced by cells carrying terminal-repeat-negative epstein-barr vrius." Journal of Virology, The American Society for Microbiology, US, vol. 79, No. 12, Jun. 1, 2005, pp. 7641-7647.
Hettich et al. "Genetic design of an optimized packaging cell line for gene vectors transducing human B cells" Gene Therapy, MacMillan Press LTD., vol. 13, No. 10, May 1, 2006, pp. 844-856.
Adhikary et al. "Standardized and highly efficient expansion of Epstein-Barr virus-specific CD4+ T cells by using virus-like particles" Journal of Virology, American Soceity for Microbiology, vol. 82, No. 8, Apr. 1, 2008, pp. 3903-3911.
International Search Report for PCT Application.: PCT/EP2011/064672, dated Oct. 14, 2011.
Ruiss et al., "A Virus-Like Particle-Based Epstein-Barr Virus Vaccine," Journal of Virology, Dec. 2011, vol. 85, No. 24, p. 13105-13113.

\* cited by examiner

SEQUENCE LISTING

<160> NUMBER OF SEQ ID NOS: 4

<210> SEQ ID NO 1
<211> LENGTH: 555
<212> TYPE: DNA
<213> ORGANISM: Artificial sequence
<220> FEATURE:
<223> OTHER INFORMATION: /note="Description of artificial sequence: LMP-1 truncated"

<400> SEQUENCE: 1

```
cttgctctcc ttctcctcct cttggcgcta ctgttttggc tgtacatcgt tatgagtgac      60
tggactggag gagccctcct tgtcctctat tcctttgctc tcatgcttat aattataatt     120
ttgatcatct ttatcttcag aagagacctt ctctgtccac ttggagcccct ttgtatactc    180
ctactgatgt caccctcctg ctcatcgctc tctggaattt gcacggacag gcattgttcc    240
ttggaattgt gctgttcatc ttcgggtgct tacttgttag gtatctggat ctacttattg    300
gagatgctct ggcgacttgg tgccaccatc tggcagcttt tggccttctt cctagccttc    360
ttcctagacc tcatcctgct cattattgct ctctatctac aacaaaactg gtggactcta    420
ttggttgatc tcctttggct cctcctgttt ctggcgattt taatctggat gtattaccat    480
ggacaacgac acagtgatga acaccaccac gatgactccc tcccgcaccc tcaacaagct    540
accgatgatt ctggc                                                      555
```

<210> SEQ ID NO 2
<211> LENGTH: 185
<212> TYPE: PRT
<213> ORGANISM: Artificial sequence
<220> FEATURE:
<223> OTHER INFORMATION: /note="Description of artificial sequence: LMP-1 truncated"

<400> SEQUENCE: 2

```
Leu Ala Leu Leu Leu Leu Leu Leu Ala Leu Leu Phe Trp Leu Tyr Ile
1               5                   10                  15

Val Met Ser Asp Trp Thr Gly Gly Ala Leu Leu Val Leu Tyr Ser Phe
            20                  25                  30

Ala Leu Met Leu Ile Ile Ile Ile Leu Ile Ile Phe Ile Phe Arg Arg
        35                  40                  45

Asp Leu Leu Cys Pro Leu Gly Ala Leu Cys Ile Leu Leu Leu Met Ser
    50                  55                  60

Pro Ser Cys Ser Ser Leu Ser Gly Ile Cys Thr Asp Arg His Cys Ser
65                  70                  75                  80

Leu Glu Leu Cys Cys Ser Ser Ser Gly Ala Tyr Leu Leu Gly Ile Trp
                85                  90                  95

Ile Tyr Leu Leu Glu Met Leu Trp Arg Leu Gly Ala Thr Ile Trp Gln
            100                 105                 110

Leu Leu Ala Phe Phe Leu Ala Phe Phe Leu Asp Leu Ile Leu Leu Ile
        115                 120                 125

Ile Ala Leu Tyr Leu Gln Gln Asn Trp Trp Thr Leu Leu Val Asp Leu
    130                 135                 140

Leu Trp Leu Leu Leu Phe Leu Ala Ile Leu Ile Trp Met Tyr Tyr His
145                 150                 155                 160

Gly Gln Arg His Ser Asp Glu His His His Asp Asp Ser Leu Pro His
                165                 170                 175
```

<210> SEQ ID NO 3
<211> LENGTH: 1158
<212> TYPE: DNA
<213> ORGANISM: Artificial sequence
<220> FEATURE:
<223> OTHER INFORMATION: /note="Description of artificial sequence:
      cDNA sequence of Epstein-Barr virus LMP-1 (strain B95.8)"

<400> SEQUENCE: 3

```
atggaacacg accttgagag gggcccaccg ggcccgcgac ggccccctcg aggaccccc       60
ctctcctctt ccctaggcct tgctctcctt ctcctcctct tggcgctact gttttggctg     120
tacatcgtta tgagtgactg gactggagga gccctccttg tcctctattc ctttgctctc     180
atgcttataa ttataatttt gatcatcttt atcttcagaa gagaccttct ctgtccactt     240
ggagcccttt gtatactcct actgatgtca ccctcctgct catcgctctc tggaatttgc     300
acggacaggc attgttcctt ggaattgtgc tgttcatctt cgggtgctta cttgttaggt     360
atctggatct acttattgga gatgctctgg cgacttggtg ccaccatctg cagcttttg     420
gccttcttcc tagccttctt cctagacctc atcctgctca ttattgctct ctatctacaa     480
caaaactggt ggactctatt ggttgatctc ctttggctcc tctgtttct ggcgatttta     540
atctggatgt attaccatgg acaacgacac agtgatgaac accaccacga tgactccctc     600
ccgcaccctc aacaagctac cgatgattct ggccatgaat ctgactctaa ctccaacgag     660
ggcagacacc acctgctcgt gagtggagcc ggcgacggac ccccactctg ctctcaaaac     720
ctaggcgcac ctggaggtgg tcctgacaat ggcccacagg accctgacaa cactgatgac     780
aatgcccac aggaccctga caacactgat gacaatggcc acatgacccc gctgcctcag     840
gaccctgaca cactgatga caatggccca caggaccctg acaacactga tgacaatggc     900
ccacatgacc cgctgcctca tagccctagc gactctgctg gaaatgatgg aggccctcca     960
caattgacgg aagaggttga aaacaaagga ggtgaccagg gcccgccttt gatgacagac    1020
ggaggcggcg gtcatagtca tgattccggc catggcggcg gtgatccaca ccttcctacg    1080
ctgcttttgg gttcttctgg ttccggtgga gatgatgacg accccacgg cccagttcag    1140
ctaagctact atgactaa                                                  1158
```

<210> SEQ ID NO 4
<211> LENGTH: 385
<212> TYPE: PRT
<213> ORGANISM: Artificial sequence
<220> FEATURE:
<223> OTHER INFORMATION: /note="Description of artificial sequence: LMP-
      1 protein of cDNA; B95.8 strain"

<400> SEQUENCE: 4

```
Met Glu His Asp Leu Glu Arg Gly Pro Pro Gly Pro Arg Arg Pro Pro
1               5                   10                  15

Arg Gly Pro Pro Leu Ser Ser Ser Leu Gly Leu Ala Leu Leu Leu Leu
            20                  25                  30

Leu Leu Ala Leu Leu Phe Trp Leu Tyr Ile Val Met Ser Asp Trp Thr
        35                  40                  45

Gly Gly Ala Leu Leu Val Leu Tyr Ser Phe Ala Leu Met Leu Ile Ile
    50                  55                  60

Ile Ile Leu Ile Ile Phe Ile Phe Arg Arg Asp Leu Leu Cys Pro Leu
```

-continued

```
            65                  70                  75                  80

Gly Ala Leu Cys Ile Leu Leu Met Ser Pro Ser Cys Ser Ser Leu
                85                  90                  95

Ser Gly Ile Cys Thr Asp Arg His Cys Ser Leu Glu Leu Cys Cys Ser
                100                 105                 110

Ser Ser Gly Ala Tyr Leu Leu Gly Ile Trp Ile Tyr Leu Leu Glu Met
                115                 120                 125

Leu Trp Arg Leu Gly Ala Thr Ile Trp Gln Leu Leu Ala Phe Phe Leu
            130                 135                 140

Ala Phe Phe Leu Asp Leu Ile Leu Leu Ile Ile Ala Leu Tyr Leu Gln
145                 150                 155                 160

Gln Asn Trp Trp Thr Leu Leu Val Asp Leu Leu Trp Leu Leu Leu Phe
                    165                 170                 175

Leu Ala Ile Leu Ile Trp Met Tyr Tyr His Gly Gln Arg His Ser Asp
                180                 185                 190

Glu His His His Asp Asp Ser Leu Pro His Pro Gln Gln Ala Thr Asp
        195                 200                 205

Asp Ser Gly His Glu Ser Asp Ser Asn Ser Asn Glu Gly Arg His His
        210                 215                 220

Leu Leu Val Ser Gly Ala Gly Asp Gly Pro Pro Leu Cys Ser Gln Asn
225                 230                 235                 240

Leu Gly Ala Pro Gly Gly Gly Pro Asp Asn Gly Pro Gln Asp Pro Asp
                245                 250                 255

Asn Thr Asp Asp Asn Gly Pro Gln Asp Pro Asp Asn Thr Asp Asp Asn
            260                 265                 270

Gly Pro His Asp Pro Leu Pro Gln Asp Pro Asp Asn Thr Asp Asp Asn
            275                 280                 285

Gly Pro Gln Asp Pro Asp Asn Thr Asp Asp Asn Gly Pro His Asp Pro
        290                 295                 300

Leu Pro His Ser Pro Ser Asp Ser Ala Gly Asn Asp Gly Gly Pro Pro
305                 310                 315                 320

Gln Leu Thr Glu Glu Val Glu Asn Lys Gly Gly Asp Gln Gly Pro Pro
                325                 330                 335

Leu Met Thr Asp Gly Gly Gly Gly His Ser His Asp Ser Gly His Gly
                340                 345                 350

Gly Gly Asp Pro His Leu Pro Thr Leu Leu Leu Gly Ser Ser Gly Ser
            355                 360                 365

Gly Gly Asp Asp Asp Pro His Gly Pro Val Gln Leu Ser Tyr Tyr
370                 375                 380

Asp
385
```

EPSTEIN-BARR-VIRUS VACCINE

This application claims priority to U.S. patent application Ser. No. 13/818,711, filed on Feb. 28, 2014 which in turn claims priority to International Application Serial No. PCT/EP/2011/064672 filed on Aug. 25, 2011, which claims benefit of U.S. Provisional Application Ser. No. 61/377,027 filed Aug. 25, 2010 and European Application No. 10008835.0 filed on Aug. 25, 2010, the contents of each application are incorporated herein by reference in their entirety.

The present invention relates to a vaccine comprising a particle, said particle comprising (i) at least one Epstein-Barr virus (EBV) structural polypeptide, (ii) at least one EBV lytic polypeptide, (iii) membrane lipids, said particle being devoid of EBV DNA, wherein (a) the B-cell transformation capacity of one or more EBV polypeptides required for B-cell transformation as comprised in said particle is disabled while their immunogenicity is maintained; and/or (b) said particle is devoid of one or more EBV polypeptides required for B-cell transformation. Furthermore, the invention relates to a method for generating a particle, to a cell obtained in the method of the invention, a kit comprising the vaccine or the particle generated according to the method of the invention. Also, the invention relates to the use of the vaccine or the particle generated according to the method of the invention for generating CD8+ cells specific for an EBV antigen.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Epstein-Barr-Virus (EBV) is an ubiquitous human herpes viruses that infects over 90% of the population world-wide with a life-long persistence in its host. In most cases, primary infection occurs during early childhood and is usually asymptomatic. In contrast, if infection is retarded and happens during adolescence or adulthood, it is regularly symptomatic, causing a benign, normally self-limiting, lymphoproliferative syndrome termed infectious mononucleosis (IM) in up to 50% of cases (Rickinson and Kieff, 2007). Although the disease is normally self-limiting, prolonged forms of IM (Tobi et al., 1982) or chronic active EBV infection (CAEBV) with fatal outcome have been reported (Lu et al., 2009: Imashuku, 2007). Clinical apparent IM has also been found to significantly increase the risk to develop Hodgkin disease and other type of lymphoma later in life (Becker et al., 2009. Goldacre et al., 2009). Today, it is also generally accepted that IM is an independent risk factor for multiple sclerosis (Thacker et al., 2006; Zaadstra et al., 2008) later in life. In addition, EBV is causally associated with a heterogeneous group of malignant diseases like nasopharyngeal carcinoma, gastric carcinoma, and various types of lymphoma (Lopes et al., 2003), so that the WHO classifies EBV as a class I carcinogen (Niedobitek, 1999).

Beside the above described medical condition caused by EBV, patients with primary or secondary immune defects like transplant recipients are at particular risk for EBV-associated diseases as a consequence of the detrimental effect of immunosuppressive agents on the immune-control of EBV-infected B-cells. EBV-associated PTLD is an important form of posttransplant complications, occurring in up to 20% of organ recipients (Everly et al 2007; Taylor et al., 2005). Importantly, immunocompromised transplant recipients who are immunologically naïve for EBV at the onset of immunosuppression are at a particular high risk of developing life-threatening EBV+ posttransplant lymphoproliferative disease (PTLD) due to a primary EBV infection, e.g. often caused after transplantation via transmission of the virus through a donor organ due to the high prevalence of EBV. Due to impaired T-cell immunity that results from exposure to immunosuppressive drugs, these patients are unable to effectively prime EBV-specific T-cells that play a critical role in controlling proliferation of EBV-infected B-cells. In contrast, patients who are EBV-seropositive at transplant have a much lower risk for developing PTLD, demonstrating the essential role of EBV-specific T-cells poised to eliminate virally infected cells. In general, patients who are EBV-seronegative before transplantation are at a much higher risk to develop EBV-associated diseases, since transmission of donor EBV in transplanted organs or natural infection with the virus causes lymphoproliferative disease in EBV-seronegative recipients after transplantation (e.g. Mendoza et al., 2006; Swerdlow et al., 2000). As with many virus-associated diseases a promising approach for preventing and/or treating virus infection and its consequences in the host is vaccination, which is also true in the case of reducing the high risk of PTLD in seronegative patients by immunizing them to EBV prior to the transplantation.

These EBV-associated diseases provide strong arguments for the development of an EBV vaccine that is both save and efficient in coping with subsequent virus infections and virus-associated diseases. First trials in humans with candidate vaccines were performed already in the 1990s using a recombinant vaccinia virus expressing the major EBV membrane antigen. BLLF-1, yielding increased titers of EBV-neutralizing antibodies (Gu et al., 1995). More recently, different peptide-based prophylactic vaccines aimed at seroconversion and prevention of IM in healthy volunteers (Elliott et al., 2008; Moutschen et al., 2007; Sokal et al., 2007) and in children awaiting kidney transplantation (Rees et al., 2009) have been described. In these children, neutralizing antibodies were detected in four recipients. However, immune responses declined rapidly and were unlikely to affect posttransplant events.

Live attenuated viruses are polyvalent vaccines that efficiently protect from infection with wild-type virus and associated diseases. Genetic attenuation is usually achieved by the serial passage of the virus in permissive cells. Unfortunately, a lytic system that allows for the spontaneous genetic attenuation does not exist for EBV, in contrast to other herpes viruses like Varizella zoster. Seroconversion by infecting people on purpose with wild-type EBV would in principle be easy but is considered unethical, as the virus is clearly oncogenic per se. Also live attenuated vaccines are usually not recommended for many groups of immunocompromised patients with primary and secondary immune deficiencies (Pickering et al., 2009) because of risks of serious side effects and disseminated infections (Duchini et al., 2003; Succi and Farhat, 2006).

Monovalent EBV vaccines relying on gp350 subunit vaccines are being studied for more than twenty years with different results: one formulation successfully induced neutralizing antibodies in healthy volunteers enrolled in a clinical phase I/II-study (Moutschen et al., 2007), whereas another vaccine formulation in children awaiting kidney transplantation has failed to influence post-transplant EBV titers and to protect from PTLD (Rees et al., 2009), probably because gp350 is usually not expressed in PTLDs and other EBV-associated malignancies. Thus, it can be doubted that a gp350 vaccine can reduce the risk to develop EBV-associated cancer.

In WO 2009/068615 the generation of virus-like particles (VLPs) is described that are characterized in that they do not comprise viral DNA or do not comprise transforming EBV DNA. Said particles are employed in an ex vivo method according to which EBV structural antigen-specific CD4+ cells are generated. Due to the potential presence of oncogenes in the DNA devoid of transforming EBV DNA and the presence of transforming proteins in the VLPs they can for safety and ethical reasons not be employed in humans. Furthermore, the generated CD4+ cells cannot be considered a potent vaccine, let alone be used as prophylactic vaccine, since only CD4+ cells have been generated from EBV-positive donors, whereas they cannot prime a an EBV-specific immune cells in an EBV-naïve individual.

The technical problem underlying the present invention was to identify alternative and/or improved means and methods that allow therapeutic and preventive vaccination against EBV infection and EBV-associated diseases.

The solution to this technical problem is achieved by providing the embodiments characterized in the claims.

Accordingly, the present invention relates in a first embodiment to a vaccine comprising a particle, said particle comprising (i) at least one Epstein-Barr virus (EBV) structural polypeptide, (ii) at least one EBV lytic polypeptide, (iii) membrane lipids, said particle being devoid of EBV DNA, wherein (a) the B-cell transformation capacity of one or more EBV polypeptides required for B-cell transformation as comprised in said particle is disabled while their immunogenicity is maintained; and/or (b) said particle is devoid of one or more EBV polypeptides required for B-cell transformation.

The term "vaccine" as employed in the present invention means to prophylactically or therapeutically immunize an individual against EBV. The vaccine according to the present invention immunizes an individual against EBV infection and EBV-associated diseases. Immunization relates to the process of stimulating and sensitizing the immune system towards the antigen(s) within the vaccine. According to the invention, prophylactic immunization refers to the first exposure of an individual's immune system, i.e. a naïve immune system, to EBV antigens. Said first exposure results in the clearance of said antigens from the body of the exposed individual and in the development of EBV-antigen specific CD4+- and CD8+-cells and antibody-producing memory B-cells. Upon a second exposure the immune system is able to prevent EBV infection and/or clear said infection more effectively thereby preventing or mitigating the development of EBV-associated diseases. Specifically, the effects of said prophylactic immunisation manifest itself in at least one of the following: preventing infection of the immunized individual with EBV, modifying or limiting the infection, aiding, improving, enhancing or stimulating the recovery of said individual from infection and generating immunological memory that will prevent or limit a subsequent EBV infection. The presence of any of said effects can be tested for and detected by routine methods known to the person skilled in the art. Preferably, the patient is challenged with one or more EBV antigens which have been part of the vaccine used and antibody titers and the number of T-cells against said one or more antigens are determined. Also, the induction of neutralizing antibodies that inhibit infection of human B-cells in vitro can be determined.

While equally provoking an immune response against EBV antigens, therapeutic immunization in accordance with the present invention is performed on individuals that have been exposed to EBV prior to said immunization, i.e. they are already infected with EBV. In this case, immunization leads to the reactivation of resting T effector cells, which are confronted with the cognate antigens in a form that these antigens are presented by professional antigen-presenting cells in association with MHC class I and/or MHC class molecules. Therapeutic immunization against EBV may prove particularly relevant in cases where the reactivation of the virus is undesirable such as, e.g. In transplant recipients or otherwise immunocompromised patients (HIV-positive individuals, cancer patients, patients with severe inflammatory or autoimmune diseases), or in cases where EBV-reactivation can lead to or has led to the development of a disease like posttransplant lymphoproliferative disorders (PTLD) and Non-Hodgkin lymphoma, chronic active EBV infection (CAEBV), oral hairy leukoplakia or in cases where the B-cell transforming capacity of EBV has led to the development of a disease such as, e.g. cancer.

Besides comprising the EBV-antigens, which according to the present invention are comprised in a particle as described in detail below, a vaccine in accordance with the invention may further comprise pharmaceutically acceptable carriers which include any carrier that does not itself elicit an immune response or any other adverse reaction harmful to the individual receiving the vaccine. Suitable carriers are typically large, slowly metabolized macromolecules such as proteins, polysaccharides, polylactic acids, polyglycolic acids, polymeric amino acids, amino acid copolymers and lipid aggregates such as, e.g. oil droplets or liposomes. Further suitable pharmaceutically acceptable carriers are well-known in the art. Additionally, said carriers may function as further immunostimulating agents which will be described in more detail below. Further, the vaccine may comprise diluents such as, e.g. water, saline, glycerol, ethanol etc. Furthermore, substances necessary for formulation purposes may be comprised in a vaccine such as emulsifying agents and/or pH buffering substances. Any combination of the above-mentioned substances may be part of a vaccine in accordance with the invention as needed.

The amount necessary and the treatment regimen for an effective immunisation may vary and depend on such factors as the individual's size, body surface area, age, sex, time and route of administration, general health, and other drugs being administered concurrently. Said effective amount is expected to be in broad range and can for any given situation be readily determined by routine experimentation and is within the skills and judgement of the ordinary clinician or physician. The mode of administration can be any mode of administration that results in the immunization of the individual exposed to the vaccine for immunization and includes parenteral administration such as, e.g., intravenous, intramuscular, intraperitoneal, intrasternal, subcutaneous, intraarticular injection or infusion and inhalation, as well as enteral administration. Preferably, the vaccine is administered at least 2 times in order to maximize the effect of the immunization.

The term "particle" as used in the present invention relates to a particulate conglomerate of EBV polypeptides and membrane lipids while being devoid of EBV DNA. The term "polypeptide" refers to molecules consisting of more than 30 consecutive amino acids. Also envisaged in accordance with the present invention is to use "peptides", i.e. molecules that comprise up to 30 amino acids, instead of polypeptides. To the extent said peptides contribute to the immunizing effect of said particle, it is understood that they comprise an EBV antigenic epitope. Also encompassed by the term "polypeptide" are fragments of polypeptides. The term "fragment of a polypeptide" refers to a portion of a polypeptide that may or may not be linked to a (biological) activity of the full-length polypeptide. Preferably, an activity is attributable to the fragment. Polypeptides may further form dimers, trimers and higher oligomers, i.e. consisting of more than one polypeptide molecule. Polypeptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "polypeptide". The terms "polypeptide" and "protein" are used interchangeably herein and also refer to naturally modified polypeptides wherein the modification is effected e.g. by glycosylation, acetylation, phosphorylation and the like. Such modifications are well known in the art. Polypeptides termed "EBV polypeptides" in accordance with the invention are polypeptides that are identical in their amino acid sequence to polypeptides of EBV. The term "EBV" as used herein relates to any wild-type, i.e. naturally occurring, EBV strain and is not restricted to one particular strain. Specifically, EBV type 1 and EBV type 2 strains are well-known in the art and have been extensively characterised. These two EBV-types differ largely in nuclear polypeptide genes that encode EBNA-LP, EBNA-2, EBNA-3A, EBNA-3B and EBNA-3C. Beyond differences relating to genes encoding polypeptides of the EBNA-family, the genomes of type 1 and 2 differ little. Type 1 is dominantly prevalent in developed world populations, whereas type 2 is also prevalent in equatorial Africa and New Guinea (Kieff and Rickinson, 2007, for review). Further, the term EBV polypeptide comprises also polypeptides that are not identical to wildtype EBV strains as regards the sequence, but comprise proteins which share at least (for each value) 99%, 98%, 97%, 96%, 95%, 90%, 85%, 80% and at least 75% identity in sequence to a wildtype EBV polypeptide. The degree of identity of polypeptide sequences can be calculated by well-known methods by the person skilled in the art and may comprise the automatic execution of algorithms effecting the alignment of sequence data and calculation of sequence homologies. The EBV polypeptides of the particle may originate from different EBV strains; preferably they originate from one strain.

As mentioned above, EBV polypeptides required to be comprised in the particle belong to the groups of EBV structural polypeptides and EBV lytic polypeptides. As will be understood by the skilled person, a particular polypeptide of EBV may belong to more than one of the above mentioned groups of polypeptides. In other words, an EBV polypeptide may represent a structural polypeptide as well as a lytic polypeptide as will be apparent from the specific EBV polypeptides mentioned in the following paragraphs. In the latter case, the particle need not comprise a further EBV polypeptide that is either a structural or a lytic polypeptide. Preferably, the particle comprises at least one separate EBV polypeptide for each of the above-mentioned groups of EBV polypeptides as this typically increases the antigenic potential of the vaccine. More preferred is that at least (for each value) 2, 3, 4, 5, 6, 7, 8, 9, 10, 11, or at least 12 separate polypeptides are independently part of each of said polypeptide groups comprised by the particle of the vaccine.

In accordance with the invention, the term "structural polypeptide" of EBV relates to polypeptides involved in the structural setup of the EBV. Said polypeptides are preferably selected from the group consisting of membrane polypeptides, tegument polypeptides and capsid polypeptides. EBV membrane polypeptides comprise the polypeptides selected from the group consisting of BALF4, BLLF1 (also termed gp350), BDLF2, BDLF3, BKRF2, BLRF1, BNLF1 (also termed LMP-1), TP (also termed LMP-2a), BXLF2, BZLF2 and any combination thereof. EBV tegument polypeptides comprise the polypeptides selected from the group consisting of BBRF2, BGLF2, BMLF1, BNRF1, BOLF1, BPLF1, BTRF1, BVRF1 and any combination thereof. EBV capsid polypeptides comprise the polypeptides selected from the group consisting of BBRF1, BcLF1, BDLF1, BFRF3 and any combination thereof. Preferably, the at least one structural polypeptide is selected from the group consisting of BLLF1, BMLF1, BNRF1 or any combination thereof such as BLLF1 and BMLF1, BLLF1 and BNRF1, or BMLF1 and BNRF1.

The term "lytic polypeptides" relates to EBV polypeptides that are involved in the induction and maintenance of the EBV lytic cycle (herein also referred to as replicative phase) and/or are expressed as a consequence of the induction of the lytic cycle. Said lytic polypeptides are preferably selected from the group comprising the immediate early genes, the early genes and the late lytic genes (Kieff and Rickinson, 2007). The lytic cycle is initiated by the expression of BZLF1 and BRLF1, both immediate early proteins, followed by the expression of the early and late proteins. Following induction, cells that have become permissive for virus replication undergo cytopathic changes characteristic of herpesviruses (Kieff and Rickinson, 2007). Exemplary lytic polypeptides to be used in accordance with the invention are selected from the group comprising BZLF1, BRLF1, BMRF1, BMLF1, BALF2, BALF5, BGL2, BHRF1, BALF4, BDLF3 and any combination thereof. Preferably, the at least one lytic polypeptide is BLLF1 (also termed gp350) or any combination thereof.

The term "membrane lipids" as used in accordance with the present invention relates to lipids that are capable of spontaneously arranging to form a lipid bilayer. Such membrane lipids are lipids that comprise a hydrophobic and a hydrophilic region, wherein after self-assembly the hydrophobic regions of the membrane lipids form the inner part of the bilayer whereas the hydrophilic regions form the outer face of the membrane. Preferably, the membrane lipids are lipids that naturally form cell membranes such as amphiphatic phospholipids. Also preferred is that said membrane lipids originate from a host cell where wildtype EBV is capable of replicating. More preferred, said membrane lipids originate from a cell according to the present invention. In accordance with the invention, the membranes comprised in the particle are present in an amount sufficient to form a membrane which constitutes the outer shell of the particle. The particle must possess said membrane outer shell, which preferably comprises at least one EBV structural polypeptide. As outlined below, preferred examples of membrane-bound EBV structural polypeptides are the gp350 polypeptide and the LMP-1 polypeptide. As further detailed below, the B-cell transformation capacity of LMP-1 may be disabled. Also preferred is that the particles membrane comprises further membrane constituents also found naturally in an EBV membrane such as, e.g. further membrane polypeptides which may be found on the inside, on the outside of the membrane or spanning the membrane.

The particle is "devoid of EBV DNA" which means the particle does not comprise EBV DNA, i.e. no EBV DNA can be detected. Specifically, the term "DNA", in accordance with the present invention, includes any DNA, such as cDNA or genomic DNA. Further included by the term "DNA" as used in this context are DNA mimicking molecules known in the art such as synthetic or semisynthetic derivatives of DNA and mixed polymers, both sense and antisense strands. Such DNA mimicking molecules or DNA derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (Braasch and Corey, 2001). LNA is an RNA derivative in which the ribose ring is constrained by a methylene linkage between the 2'-oxygen and the 4'-carbon. They may contain additional non-natural or derivatized nucleotide bases, as will be readily appreciated by those skilled in the art. Accordingly, the particle must not comprise DNA sequences that are identical to EBV DNA sequences, wherein said sequences preferably relate to EBV gene sequences. Furthermore, the particle must not comprise nucleic acid sequences that share at least a (for each value) 99%, 98%, 97%, 96%, 95%, 90%, 85%, 80% and at least 75% sequence identity to a wildtype EBV nucleic acid sequence. The degree of sequence identity of nucleic acid sequences can be calculated by well-known methods by the person skilled in the art and may comprise the automatic execution of algorithms effecting the alignment of sequence data and calculation of sequence homologies. Also, the particle may not comprise a DNA sequence that upon expression generates a polypeptide that functionally resembles an EBV polypeptide, wherein the functional resemblance preferably concerns B-cell transformation capacity. Methods to test functional similarity of polypeptides include in silica as well as in vitro, ex viva and in vivo tests that are well-known to the skilled person in the art. For example, to determine functional resemblance one can generate deletion mutants of EBV and perform complementation analysis. Specifically, a deletion mutant of EBV is characterised in that the sequence of a gene that encodes, e.g. a polypeptide that is essential in B-cell transformation, is deleted. As a result, said deletion mutant is not capable of transforming B-cells. To test the functional resemblance of a DNA sequence to the deleted EBV sequence, said DNA to be tested is supplied to the deletion mutant, e.g., by incorporation of said DNA to be tested into the genomic DNA of said deletion mutant. Subsequently, it is determined whether the thus modified deletion mutant is capable of transforming B-cells, i.e. complements the deletion and results in an EBV that functionally resembles a wildtype EBV. Variations of said complementation analysis are known in the art and can further be adapted to the specific needs of the skilled person on the basis of his technical knowledge in the field.

In a further embodiment it is envisaged that no DNA of any kind is comprised in se vaccine or the particle comprised in the vaccine.

The particle may, however, comprise EBV RNA. It is understood that the term "RNA" as used herein comprises all forms of RNA including mRNA, ncRNA (non-coding RNA), tRNA and rRNA. The term "non-coding RNA" includes naturally occurring siRNA (small interfering RNA), miRNA (micro RNA), rasiRNA (repeat associated RNA), snoRNA (small nucleolar RNA), and snRNA (small nuclear RNA). Viral mRNA when comprised in the particle as described herein in various embodiments could be translated in infected cells and peptides derived from the translated polypeptides could be presented in association with MHC class I antigens such that they prime or reactivate CD8+ T cells. Corresponding EBV viral mRNA are mRNA molecules whose transcripts are mentioned above to belong EBV "structural polypeptides and "lytic polypeptides". For example, the particle may comprise viral EBV mRNA encoding BALF4, BLLF1 (also termed gp350), BDLF2, BDLF3, BKRF2, BLRF1, BNLF1 (also termed LMP-1), TP (also termed LMP-2a), BXLF2, BZLF2, BBRF2, BGLF2, BMLF1, BNRF1, BOLF1, BPLF1, BTRF1, BVRF1, BBRF1, BcLF1, BDLF1, BFRF3 (as "structural polypeptides"); and/or BZLF1, BRLF1, BMRF1, BMLF1, BALF2, BALF5, BGL2, BHRF1, BALF4, BDLF3 (as "lytic polypeptides"); and/or corresponding polypeptides whose transformation capacity has been disabled while their immunogenicity is maintained. Preferably, the EBV viral mRNA molecule(s) comprised in the particle in accordance with the invention encode the preferred "structural polypeptides and/or "lytic polypeptides" and/or corresponding polypeptides whose transformation capacity has been disabled while their immunogenicity is maintained or preferred combinations thereof described herein above as being comprised in a particle or constituting it. In other words, the transcripts of the mRNA molecules comprised in the particle mirror the EBV polypeptide composition of the particle according to the invention. It is equally envisaged that the particle may—alternatively or additionally—comprise EBV mRNA whose transcript is not comprised in the particle. For example, mRNA encoding BZLF1 and/or BRFL1 can be comprised in a particle in accordance with the invention while BZLF1 and/or BRLF1 polypeptides are not comprised in said particle. It is also envisaged that the particle does not comprise an mRNA molecule encoding every polypeptide comprised in the particle according to the invention, i.e. mirroring the EBV polypeptide composition of said particle. Preferably, at least BRLF1 and/or BZLF1 encoding EBV mRNA is comprised in the particle according to the invention. The incorporation of mRNA into said particle can be achieved, e.g., with the method described herein below in which EBV mRNA molecules present in the cell expressing the modified EBV genome are incorporated into particles. Further methods for incorporating EBV mRNAs into the particles according to the invention include, e.g., electroporation, lipofection or other methods known in the art to effect the transfer of nucleic acids through a lipid membrane. It is understood in accordance with the invention that any mRNA molecule(s) present in the particle of the invention is/are not capable to induce transformation of the infected cell into a proliferative state. It is understood by the person skilled in the art that the expression of potentially transforming EBV polypeptides from said EBV mRNAs comprised in the particle will not be sufficient to induce transformation of an infected cell due to the instability of mRNA molecules and the resulting low rate of expressed EBV polypeptides. Nevertheless, the skilled person is in the position to determine which mRNAs he can use and/or what kind of modifications to corresponding EBV mRNAs have to be effected to exclude the expression of EBV polypeptides having transforming activity alone or in combination with further EBV polypeptides, should this be necessary for regulatory purposes in the process of approval as active agent of a pharmaceutical.

In another embodiment it is envisaged that no RNA of any kind is comprised in the vaccine or the particle comprised in the vaccine.

Furthermore envisaged is that no nucleic acid of any kind is comprised in the vaccine or the particle comprised in the vaccine.

This absence of at least EBV DNA from the particle is owed to the capacity of wildtype EBV to transform B-cells into cells that are capable of indefinite growth. This is due to the presence of potential oncogenes in the wildtype EBV genome, i.e. genes that are involved in the development of cancer. Therefore, and with regard to safety of the vaccine of the invention upon administration to the individual to be immunized, exclusion of EBV DNA from the vaccine, more specifically from the particle, results in the minimisation of the risk of said individual to be immunized to experience B-cell transformation or develop cancer as a direct consequence of the vaccination. This is particularly important in the case of individuals which have not been exposed to and infected by EBV previously; see the introductory part herein above.

As a further feature that increases the safety of the vaccine upon administration while contributing to immunogenicity, the particle may comprise one or more EBV polypeptides required for B-cell transformation whose B-cell transformation capacity is disabled while their immunogenicity is maintained. In vitro, B-cell transformation by EBV leads to proliferation of infected B-cells for extended life-spans. The term "required for B-cell transformation" means in accordance with the invention that the said one or more EBV polypeptides are essential in transforming B-cells upon infection with a wildtype EBV. In other words, in the absence of said one or more essential EBV polypeptides a B-cell is not transformed upon infection. Accordingly, the particle upon fusion with the B-cell is incapable of transforming the B-cell. While it may suffice to disable the B-cell transformation capacity of one essential EBV polypeptide in order to exclude the possibility of B-cell transformation, one can alternatively disable the B-cell transformation capacity of an essential combination of EBV polypeptides to achieve the same result achieved when only one essential polypeptide is disabled, i.e. achieve the exclusion of the possibility of B-cell transformation. Preferably, the B-cell transformation capacity of more than the one essential EBV polypeptide or the essential combination of EBV polypeptides is disabled. Corresponding EBV polypeptides that are essential in B-cell transformation are EBNA2, LMP1, EBNA-LP. Disabling the B-cell transformation capacity of one of these EBV polypeptides is sufficient to exclude the possibility of B-cell transformation. Essential combinations of EBV polypeptides that are required for B-cell transformation are EBNA3A and EBNA3C, LMP-2A and EBNA3A, or LMP-2A and EBNA3C. As will readily be understood by the skilled person if only one member of a corresponding essential combination is present in the particle, its B-cell transformation capacity must be disabled since on its own it is still capable of transforming a B-cell. This equally applies to the presence of more members of a combination as long as the combination is not complete, i.e. not all members required to exclude the possibility of B-cell transformation are present in the particle. In other words, only when all members of an essential combination are disabled, then the possibility of B-cell transformation is excluded.

It is understood that, in order to ensure safety of the vaccine, a particle comprising said one or more EBV polypeptides required for B-cell transformation whose B-cell transformation has been disabled does not at the same time comprise the corresponding functional EBV polypeptide counterpart.

The above applies mutatis mutandis for the below embodiments.

Disabling the capacity to transform B-cells can be achieved by methods such as modifying the polypeptide's domain that is functionally involved in the process of B-cell transformation. Said modifying can be achieved by methods such as, e.g. deletion of said functional domain or parts thereof, steric inhibition of said functional domain or the entire polypeptide, or substitution of one or more amino acids of said functional domain to the effect that function is compromised. When disabling a polypeptides B-cell transformation capacity, its immunogenicity is to be maintained. The person skilled in the art is in the position to determine without further ado the antigenic regions of a protein and specific antigenic epitops within said regions by employing in silico as well as in vivo, in vitro or ex vivo routine experimental methods. After determination of said antigenic region he is in the position to choose a strategy that is suitable to maintain the immunogenicity of a polypeptide while disabling its B-cell transformation capacity. This way, one can obtain functionally disabled but immunogenic EBV polypeptides. For example and in the case of transmembrane polypeptides having a B-cell transformation capacity such as, e.g., LMP-1 (also termed BNLF1), one can truncate said polypeptide by deleting only the transmembrane portion of said polypeptide but preserving the extramembranous part of said polypeptide on the outside of the virus particle.

Alternatively or in addition, the particle may be devoid of one or more EBV polypeptides that are required for B-cell transformation. Any of the above-mentioned EBV polypeptides required for B-cell transformation or EBV polypeptide combinations required for B-cell transformation may be lacking from the particle. Nevertheless and in accordance with the invention, the particle is still immunogenic due to the presence of other EBV particles such as the at least one EBV structural polypeptide and the at least one EBV lytic polypeptide. In the case where one or more transforming polypeptides are lacking and at least one EBV polypeptide is disabled, it is understood that the one or more EBV polypeptide that is lacking cannot be disabled at the same time. In other words, if said one or more EBV polypeptides is disabled, it cannot be lacking at the same time. If a combination of EBV polypeptides is essential in B-cell transformation, a first member of the combination may be disabled while a second member may be lacking.

The definitions and explanations provided for this embodiment apply mutatis mutandis for all of the below embodiments unless explicitly stated otherwise.

In general and also in accordance with this invention, it is desirable that the vaccine comprises as many different EBV polypeptides as possible in order to maximize the antigenic potential of the vaccine. Therefore, the present invention relates in an alternative embodiment to a vaccine comprising a particle, said particle comprising a modified EBV, wherein said modified EBV in comparison to a wildtype EBV is devoid of EBV DNA, and wherein (a) the B-cell transformation capacity of one or more EBV polypeptides required for B-cell transformation as comprised in said particle is disabled while their immunogenicity is maintained; and/or (b) said particle is devoid of one or more EBV polypeptides required for B-cell transformation.

In a preferred embodiment of said alternative embodiment, said modified EBV differs from wildtype EBV only with respect to the above-identified features.

This alternative embodiment realizes the full antigenic capacity of the wildtype EBV but excludes the potential of the vaccine to induce B-cell transformation or other EBV-associated diseases such as, e.g., infectious mononucleosis (IM), tumors, in the individual to be immunized. As a consequence, the immunized individual's immune system has been primed in response to a broad range of EBV antigens in the vaccine closely resembling the wildtype EBV thus resulting in modulation of the immune system that is from a medical point of view considered to be very effective in battling EBV infections.

In a more preferred embodiment of said alternative embodiment, said modified EBV differs from wildtype EBV in addition in that the EBV polypeptides EBNA-2, EBNA-3a, EBNA-3b, EBNA-3c are lacking. Even more preferred is that LMP-1 is disabled and/or that BZLF1 is part of the modified EBV.

The particles comprised in the vaccine of the invention can be prepared by methods well-known in the art involving standard cloning and cell culture techniques and described, e.g. in Sambrook, Molecular Cloning A Laboratory Manual, Cold Spring Harbor Laboratory (1989) N.Y., "Practical Cell Culture Techniques", Boulton at Baker (eds), Humana Press (1992), ISBN 0896032140; "Human Cell Culture Protocols", Gareth E. Jones, Humana Press (1996), iSBN 089603335X. For example, the EBV polypeptides can be recombinantly generated by expression from DNA sequences within host cells that allow aggregation and egress of the particles. Said particles can also be produced partially or entirely on synthetic basis. Preferably, the particle is prepared by any of the below detailed methods.

Although EBV is causally implicated in a variety of severe medical conditions as outlined above and despite intense research and successes with regard to battling different virus strains, the development of an EBV vaccine has thus far failed, albeit recent years have seen the approval of virus vaccines against, e.g., human papilloma virus as well as hepatitis B. The present inventors have been able to generate for the first time a vaccine that is effective in priming an EBV-specific immune response in EBV-naïve individuals as well as in reactivating the EBV-specific immune response in EBV-positive individuals and thus provides the answer to the long-felt need for an EBV vaccine.

Most surprising the vaccine of the invention was able to elicit an EBV-specific CD8+ immune response, i.e. a cellular immune response in addition to a potent humoral immune response, in an animal model and to reactivate EBV-specific CD8+ T cells from EBV-seropositive human donors although the EBNA3 polypeptides have been deleted due to their B-cell transformation capacity. This is surprising since it is well-known that the CD8+ cells generated upon EBV infection are predominantly directed towards EBNA3 polypeptides and one would have expected that a vaccine devoid of said EBNA3 polypeptides does not result in a potent EBV-specific CD8+ cell response. Furthermore, human B-cells, which are the targets for the EBV vaccine of the invention, are supposed not to have the potential to cross-present MHC class I-restricted epitopes derived from viral particles (Keller et al., 2009).

The inventors used a cell line which carries an EBV helper genome that was modified such that it cannot be packaged into the particles being part of the vaccine of the invention. To further ensure the safety of the vaccine, the vaccine is preferably devoid of EBV polypeptides that can transform B-cells as a result of a preferably accordingly modified EBV (helper) genome in the host cell line. Thus, even in the rare case that an EBV helper genome would illegitimately be packaged into a particle, transformation of a B-cell and re-activation of the virus can be completely excluded.

In summary, the inventors provide particles that are free of viral DNA and reliably induce strong polyvalent neutralizing humoral and cellular immune responses in nave hosts. They thus constitute an effective and safe vaccine for individuals having any kind of serostatus, in particular for EBV-naïve patients awaiting e.g. transplantation where they reduce the risk of EBV-associated diseases in immunocompromised patients.

In a preferred embodiment of the vaccine of the invention, said particle comprises at least one EBV polypeptide selected from BZLF1 and gp350 and/or further comprises at least one EBV latent polypeptide.

The EBV polypeptide gp350 (glycoprotein 350) is a membrane bound glycoprotein. Said gp350 is responsible for the specificity (tropism) for B cells by binding to CD21 on the cell surface of B-cells. Additional accessory viral polypeptides may contribute to a fully efficient infection (Chesnokova et al., 2009; Omerovic et al., 2005; Silva et al., 2004; Sorem and Longnecker, 2009). Also, infection at low efficiency has also been demonstrated with recombinant EBV particles devoid of gp360 (Janz et al., 2000). Recent research also postulates an implication of gp350 after the internalization step and presumably during release of the viral capsid from the endosomal compartment (Busse et al., 2010). While not crucial for the vaccine according to the invention, it is preferred that gp350 is comprised in the particle's membrane since upon administration of the vaccine the immune response generated more closely resembles the immune response elicited upon infection by a wildtype EBV.

The EBV immediate early polypeptide BZLF1 mediates the disruption of latent EBV infection and is generally considered the key regulator in the induction of the lytic phase of EBV. In wildtype EBV, BZLF1 is not constantly expressed. Upon entering the host's body. BZLF1 is not expressed, only after B-cell infection BZLF1 is expressed resulting in the induction of the lytic cycle. The lytic cycle is maintained until the immune response of the host is adapted to EBV and is able to contain the infection which is the moment when EBV enters the latent phase of infection. In said phase BZLF1 is not expressed. The persistent infection with EBV is characterised in that there is an alternation of lytic and latent phase, wherein the induction of the lytic phase is due to the expression of BZLF1 which is at these times presented to immune cells. Thus, a vaccine that comprises BZLF1 primes the immune system of the immunized individual so that it is mobilized prior to the actual egress of new virus particles as a result of the induction of the lytic phase.

The term "latent polypeptides" relates to EBV polypeptides that are involved in the induction and maintenance of the EBV latent cycle and/or are expressed as a consequence of the induction of the latent cycle. Preferably, the at least one latent polypeptide is LMP-1 (also termed BNLF1) and/or LMP-2.

The invention also relates to a method for generating a particle, comprising the steps of (a) transfecting a cell with a modified EBV genome, wherein said modified EBV genome in comparison to a wildtype EBV genome at least (aa) lacks one or more sequences that are required for the packaging of said wildtype EBV genome, lacks one or more sequences encoding EBV polypeptides required for said packaging and/or comprises one or more sequences encoding EBV polypeptides whose packaging capacity is disabled; (ab) lacks one or more sequences encoding EBV polypeptides that are required for B-cell transformation and/or comprises one or more sequences encoding EBV polypeptides whose B-cell transformation capacity is disabled; and (ac) lacks one or more sequences encoding EBV polypeptides that are required for inducing replication of an EBV and/or comprises one or more sequences encoding EBV polypeptides whose capacity for inducing EBV replication is disabled; (b) culturing the cell obtained in step (a) under conditions that allow expression of said modified EBV genome; (c) inducing the replicative phase of EBV; and (d) isolating said particle.

The term "transfection" is used in connection with the invention according to the accepted meaning in the art, viz. the process of introducing nucleic acids into cells. Transfection can be achieved by a variety of methods such as, e.g. chemical-based methods like calcium phosphate-mediated transfection or liposome-mediated transfection. Also non-chemical methods like electroporation sonoporation or particle-based methods such as gene-gun-mediated transfection or magnetofection as well as viral-mediated methods are known in the art.

The "modified EBV genome" is modified in comparison to a wildtype EBV genome. As outlined in the above sections, several wildtype EBV strains exist whose genetic make-up is well-known in the art (Rickinson and Kieff, 2007). As is apparent from the above, the modified EBV genome is modified only with regard to sequences that are common to all EBV strains. The term "packaging" is well-known in the art with regard to virus assembly and relates to the process of introducing the linear EBV viral DNA into the virus particle during virus particle assembly. The packaging of EBV genomic DNA initiates at sequences (TR) that are directly repeated at both ends of said genomic DNA. Specifically, said modified EBV genome lacks one or more sequences that are required for packaging of a wildtype EBV genome. The term "required for packaging" means in accordance with the invention that said one or more sequences are essential in packaging EBV DNA into a wildtype EBV particle. In other words, in the absence of said one or more sequences the EBV DNA is not packaged into a wildtype EBV particle and a particle generated by the method of the invention that may also be comprised in the vaccine of the invention. Accordingly, the modified EBV genome is not packaged into a particle as described herein when said one or more sequences required for packing are lacking. For example, the sequences of the terminal repeats of EBV can be deleted. Said terminal repeats are recognized by an enzyme termed "terminase". Alternatively or additionally, one can delete one or more sequences encoding EBV polypeptides required far said packaging. Such EBV polypeptides are, e.g., the enzyme terminase. Also, said EBV polypeptide(s) required for said packaging may be disabled so that they lose their packaging capacity. Said disabling can be achieved by methods such as modifying the polypeptide's domain that functionally involved in the process of packaging. Said modifying can be achieved by methods such as, e.g., deletion of said functional domain or parts thereof, steric inhibition of said functional domain or the entire polypeptide, or substitution of one or more amino acids of said functional domain.

While it may suffice to delete one sequence required for packaging or one sequence encoding an EBV polypeptide required for said packaging and/or to disable the packaging capacity of one essential EBV polypeptide in order to exclude the possibility of packaging, one can alternatively disable the packaging capacity of a combination of EBV polypeptides also resulting in the exclusion of the possibility of EBV DNA packaging.

Further, the modified EBV genome lacks one or more sequences encoding EBV polypeptides that are required for B-cell transformation and/or comprises one or more sequences encoding EBV polypeptides whose B-cell transformation capacity is disabled. Specific EBV polypeptides and combinations thereof have been described herein above. The skilled person is the position to directly and unambiguously identify the genomic sequences encoding said one or more polypeptides. He is furthermore in the position to carry out those steps that lead to the deletion of said one or more sequences from an EBV genome and/or to modify said one or more sequences leading to one or more EBV polypeptides whose transformation capacity is disabled upon expression.

Also, the modified EBV genome lacks one or more sequences encoding EBV polypeptides that are required for inducing replication of an EBV and/or comprises one or more sequences encoding EBV polypeptides whose capacity for inducing EBV replication is disabled. EBV polypeptides that are involved in the replication of EBV are mostly polypeptides termed lytic polypeptides that are involved in the replication of the viral genome as well as in the expression of the EBV genome finally resulting in the egress of virus particles from the infected host cell. The term "required for" has the same meaning as explained herein above for other polypeptides, i.e. one or more polypeptides are absolutely necessary with regard to a specific aspect, in this aspect of the invention, the presence of said one or more sequences encoding EBV polypeptides is absolutely necessary for the induction of the replication of EBV. Corresponding polypeptides can be selected from the following group consisting of BZLF1, BRLF1, BMLF1 and combinations thereof. Also in this regard the person skilled in the art is in the position to directly and unambiguously identify the genomic sequences encoding said one or more polypeptides as well as to carry out those steps that lead to the deletion of said one or more sequences from an EBV genome and/or to modify said one or more sequences leading one or more EBV polypeptides whose capacity for inducing EBV replication is disabled upon expression.

The term "culturing" is used in accordance with its accepted meaning in the art. Generally, cell culture methods, such as, for example, media constituents, marker choice and selection, cell quantification and isolation, are methods well-known in the art and described, for example, in "Practical Cell Culture Techniques", Boulton et Baker (eds), Humana Press (1992), ISBN 0896032140; "Human Cell Culture Protocols", Gareth E. Jones, Humana Press (1996), ISBN 089603335X and exemplarily in the example section. Culture conditions vary from cell-type to cell-type and moreover, can result in different phenotypes being expressed for a particular cell-type. Generally, cells are grown and maintained at an appropriate temperature and gas mixture, i.e. typically 37° Celsius, 5% $CO_2$, in growth media (a) as irrigating, transporting and diluting fluid while maintaining intra- and extra-cellular osmotic balance, (b) that provides cells with water and certain bulk inorganic ions essential for normal cell metabolism, (c) which—combined with a carbohydrate, such as glucose—provides the principle energy source for cell metabolism and (d) which provides a buffering system to maintain the medium within physiologic pH range, i.e. cells are kept viable. The recipe of growth media vanes greatly depending on cell-type and contains, for example and without limitation, growth factors, nutrient components, glucose, buffers to maintain pH and antifungizides and -biotics. Methods for culturing and maintaining cells in culture are well-known in the art; growth media and other cell culture related material as well as instructions and methods for successful culturing of cells can, for example, be obtained at Sigma-Aldrich or Invitrogen. The conditions to allow expression of the modified EBV genome correspond essentially to the general conditions described herein above. Modifications to enhance polypeptide expression from the EBV genome in the host cell are known to the person skilled in the art.

Cells to be used in the method of the invention are preferably cells of human origin. Preferred is the use of the HEK293 cell line which can be obtained, e.g., from the German Collection of Microorganisms and Cell Cultures (DSMZ, Braunschweig) or from the American tissue culture collection (ATCC).

The term "inducing the replicative phase" of EBV means in accordance with the present invention the initiation of the process that ultimately leads to intracellular assembly of virus-like particles (VLPs) and egress of said VLPs as particles defined herein. The induction can be achieved, for example, by complementing the cell with said one or more EBV polypeptides that are absent from the host cell due to the deletion of said one or more sequences encoding EBV polypeptides that are required for inducing replication and/or the modification of said one or more sequences encoding EBV polypeptides resulting in their inability to induce EBV replication. Said complementation can be achieved e.g. by providing the cell with said deleted one or more sequences, e.g. on a plasmid (stably or transiently transfected), from which the missing EBV polypeptides can be expressed; or by providing the cell with one or more unmodified sequences encoding functional EBV polypeptides that are capable of inducing the replicative phase. The provision of said one or more DNA sequences can be effected by methods as described herein above and in the example section. Alternatively, said complementation can be achieved by providing the cell said one or more EBV polypeptides required for inducing replication of an EBV. The provision of said one or more polypeptides to the cell can be achieved by protein delivery methods that are well-known in the an and may involve the use of reagents such as, e.g., Proteo-Juice™ (Merck), TurboFect™ (Fermentas) or Lipodin-Pro™ (Abbiotec).

The thus generated particle(s) can upon egress from the host cell be collected from or as part of the cell culture supernatant. For example, the supernatant comprising said generated particles can be used directly for the infection of B-cells, or said particles can be further concentrated by ultracentrifugation or ultrafiltration.

The particle generated according to the method of the invention is suitable to be used in the vaccine of the present invention. Preferably, the particle comprised in the vaccine of the invention is generated according to the method of the invention which may involve further modification to the EBV genome in comparison to a wildtype EBV genome which the skilled person can effect without further ado on the basis of his common general knowledge in the field of biotechnology as well as on the basis of the methods described and/or referred to herein.

In a preferred embodiment, a polypeptide whose transformation capacity is disabled in (a) of the vaccine of the invention or in (ab) of the method of the invention is the LMP-1 polypeptide.

The LMP-1 EBV polypeptide is a membrane spanning polypeptide that is required for B-cell transformation. LMP-1 mimics a constitutively active CD40 receptor (Gives et al., 1997). The B-cell transformation capacity can, e.g., be disabled by truncation of said polypeptide by deleting only the membrane-bound portion of said polypeptide or parts thereof and preserving the extramembranous part of said polypeptide on the outside of the virus particle. A corresponding method is disclosed in the Example section. Briefly, LMP-1 was inactivated by only deleting its hydrophobic region, i.e. amino acids 26 to 210 (of SEQ ID NO.: 4) comprising the transmembrane domain, while in an effort to maintain its immunogenicity the extra-membrane part was conserved. Thus, in a preferred embodiment, the truncated LMP-1 is encoded by the DNA sequence of SEQ ID NO.: 1 and consists of the polypeptide sequence of SEQ ID NO.: 2.

In another preferred embodiment of the vaccine or method of the invention, the one or more EBV polypeptides required for B-cell transformation which are lacking according (b) of the vaccine of the invention or (ab) of the method of the invention are selected from the group consisting of EBNA-2, EBNA-3a, EBNA-3b and EBNA-3c.

In a further preferred embodiment of the method of the invention, the one or more EBV polypeptides that are required for inducing replication of an EBV which are lacking or said one or more EBV polypeptides whose capacity for inducing EBV replication is disabled according to the method of the invention in step (ac) are selected from the group consisting of BZLF1, BRLF1, BMLF1 and any combination thereof and wherein in step (c) of said method of the invention the replicative phase is induced by providing to said cell the selected polypeptide(s).

In a more preferred embodiment of the method of the invention, the selected polypeptide is BZLF1.

In an even more preferred embodiment of the method of the invention, said provision of said one or more EBV polypeptides or said BZLF1 to said cell is effected by expression of said one or more EBV polypeptides or said BZLF1 from a stably transfected vector in said cell.

While there exist several methods to provide the cell with said one or more EBV polypeptides or said BZLF1 as outlined above, the expression from a stably integrated plasmid is advantageous for several reasons. The expression levels of the polypeptide(s) expressed are consistent, the modulation of the host cell is reduced to the minimum and the technical complexity of producing said particles is equally significantly minimized which in the case of large scale production systems is advantageous.

In a most preferred embodiment of the method of the invention, the expression of said one or more EBV polypeptides or said BZLF1 is inducibly regulated.

Techniques to control expression of polypeptides from a plasmid are well-known in the art. One technique involves the use of inducible promoters such as, heat, chemical, or light sensitive promoters. For example, tetracycline inducible promoters, Dox-inducible promoters, ecdysone inducible promoters or heavy metal inducible promoters are known in the art can be used in accordance with the invention (see, e.g., FIG. 7). Further suitable promoters are well-known to the person skilled in the art. Alternatively, BZLF1 can also he regulated when fused to the estrogen receptor and is thus activated upon the addition of estrogen.

In another preferred embodiment of the method of the invention, said method comprises after step (b) and prior to step (c) a further step (b') comprising: providing one or more viral or non-viral polypeptides, one or more viral or non-viral nucleic acid sequences and/or one or more vaccine adjuvants to said cell, wherein said one or more viral polypeptides or said one or more viral nucleic acid sequences are not EBV polypeptides or EBV nucleic acid sequences, respectively.

The one or more viral or non-viral polypeptides, one or more viral or non-viral nucleic acid sequences can be of any origin or sequence as long as they are not EBV polypeptides or EBV nucleic acid sequences according to the definition given herein above. Preferably, said one or more polypeptides or said one or more nucleic acid sequences are polypeptides or sequences that are immunogenic, i.e. elicit a specific immune response, and, more preferred, have been shown to be safe and effective as immunizing agent.

The term "adjuvant" is used according to the well-known meaning in connection with vaccines. Specifically, an adjuvant is an immunological agent that modifies, preferably enhances, the effect of a vaccine while having few if any direct effects on the immune system when given per se. In accordance with the present invention it is defied as any substance that is capable of accelerating, prolonging or enhancing antigen-specific immune responses when used in combination with specific antigens. Suitable adjuvants can be inorganic adjuvants such as, e.g., aluminium salts (e.g., aluminium phosphate, aluminium hydroxide), organic adjuvants such as squalene or oil-based adjuvants, as well virosomes.

This embodiment is owed to the fact that the particle generated according to the invention can effectively encompass other polypeptides than EBV polypeptides as well as nucleic acid sequences and therefore besides being a vaccine act as delivery tool for further compounds to be delivered to the individual to be immunized. Incorporation of said one or more viral or non-viral polypeptides, one or more viral or non-viral nucleic acid sequences and/or one or more vaccine adjuvants can conveniently be achieved by the provision of the latter to the cell in accordance with the above described techniques such as protein transfection or nucleic acid transfection in amounts that are suitable for said incorporation. The specific amounts required as well as the specific technique to achieve said intracellular levels can be experimentally determined without undue burden by the skilled person.

In a preferred embodiment of the vaccine of the invention, it additionally comprises one or more viral or non-viral polypeptides, one or more viral or non-viral nucleic acid sequences and/or vaccine adjuvants, wherein said one or more viral polypeptides or said one or more viral nucleic acid sequences are not EBV polypeptides or EBV nucleic acid sequences, respectively.

The definitions given above apply also to this embodiment and methods to generate said particles have equally been described above. Preferably, said particle as comprised in the vaccine comprises one or more viral or non-viral polypeptides, one or more viral or non-viral nucleic, acid sequences and/or vaccine adjuvants are part of the particle. Nevertheless, it is also envisaged that said vaccine comprises one or more viral or non-viral polypeptides, one or more viral or non-viral nucleic acid sequences and/or vaccine adjuvants that are admixed to the particles defined herein without being incorporated into said particles.

Another embodiment of the invention relates to a cell obtained by transfecting according to step (a) of the method according to the invention.

As will be understood by the skilled person in the art and as outlined above, the stable transfection of a vector enabling the preferably inducibly regulated expression of said one or more EBV polypeptides or said BZLF1 is particularly useful in large scale setups and/or setups that require a product that is standardized and consistent with regard to its quality. This is conceivably important for products that are intended for medical use, specifically for administration to patients, such as the particle generated according to the method of the invention which is, preferably part of the vaccine of the invention. Preferably, the cell is a cell in culture, a cell line or a cell in vitro.

In another embodiment, the invention relates to a kit comprising a vaccine according to the invention or a particle generated according to the method of the invention.

The kit may comprise only one kind of an item such as the vaccine of the invention or a particle generated according to the method. It may also comprise the various components making up a vaccine according to the invention.

In a preferred embodiment, the particle and pharmaceutically acceptable carriers making up a vaccine are comprised in a kit according to the invention as separate components.

In another preferred embodiment, the cell obtained according to the method of the invention and the compound(s) required for inducing the replicative phase are comprised in a kit according to the invention as separate components. Accordingly, the various components of the kit may be packaged in one or more containers such as one or more vials. The vials may, in addition to the components, comprise preservatives or buffers for storage, media for maintenance and storage, e.g. cell media, DMEM, MEM, HBSS, PBS, HEPES, hygromycin, puromycin. Penicillin-Streptomycin solution, gentamicin inter alia. Advantageously, the kit further comprises instructions for use of the components allowing the skilled person to conveniently work, e.g., various embodiments of the invention. Any of the components may be employed in an experimental setting. For example, the particle per se or the vaccine may be used to study the immune response of in animal as well as human studies.

Also, the invention relates to the use f a vaccine according to the invention or a particle obtained by the method of the invention for generating CD8+ T cells specific for an EBV antigen.

The use according to the invention may be implemented, e.g., according to method described below.

Additionally, the invention relates to a method for generating a preparation containing CD8+ T cells specific for an EBV antigen, the method comprising the steps of: (a) incubating B-cells with a vaccine according to the invention or a particle obtained by the method of the invention for a period of time sufficient to generate a preparation containing B-cells presenting EBV antigens; (b) admixing said B-cells obtained in step (a) with a preparation comprising T cells; and (c) incubating said admixture obtained step (b) to generate preparation including CD8+ T cells specific for an EBV antigen.

The term CD8+ T cells can interchangeably be used with the term cytotoxic T cells which is also well-known in the art.

The term "incubating" refers in accordance with this embodiment to the process of bringing into contact different entities. With regard to incubating B-cells with a vaccine of the invention or a particle obtained by the method of the invention, said incubation is performed for a specific period of time under conditions that keep the B-cells viable and reactive to antigens such as said vaccine or particle. The time period necessary for antigen presentation by the B-cells can be experimentally determined and may vary depending an the experimental setup chosen. Preferably, the incubation is maintained for at least (for each value) 2, 4, 6, 8, 16 or at least 24 hours. Also envisaged are incubation times of at least 2, at least 3 or at least 4 days.

The preparation of T cells that are admixed with the B-cells in step (comprises nave T cells and/or EBV-specific memory and/or EBV-specific effector T cells. The incubation step (c) of the method of the invention must be for a period of time to allow generation of EBV-specific CD8+ T cells. Said time period necessary for CD8+ T cell development can be experimentally determined and may vary depending on the experimental setup chosen. Preferably, the incubation is maintained for at least (for each value) 2, 4, 6, 8, 16 or at least 24 hours. Also envisaged are incubation times of at least 2, at least 3 or at least 4 days. The method or the use can be an in vivo, ex vivo or in vitro method or use.

This embodiment of the invention is owed to the surprising finding that, contrary to a well-established dogma in the art (e.g., Keller et al., 2000 WO 2009/068615), B-cells are capable of cross-presentation and cross-priming. Specifically, cross-priming describes the process by which an antigen alter uptake by an immune cell is processed for MHC class-I and MHC class II-associated presentation. Said process was previously believed to be restricted to, e.g., dendritic cells and macrophages. While MHC class II-associated antigen presentation results in the generation of CD4+ T MHC class I-associated antigen presentation results in the generation of CD8+ antigen specific T killer cells. B-cells are believed to be incapable of cross-priming, their main function being the generation of antibodies. The inventors of the present invention could surprisingly show that upon administration of a particle as described he-rein to mice the presence of EBV specific T cells could be shown in splenocytes (cf., e.g., Example 4, FIG. 5; Example 8, FIG. 11C).

The figures show:

FIG. 1: The 293-VII+ helper genome contains several deletions (represented by the triangles). The latent genes EBNA-2, EBNA-3a, -3b, and -3c were entirely deleted. LMP-1, which has been described to be present in virus particles, was functionally inactivated by deleting the transmembrane domain. Also removed were BZLF-1, which activates the lytic cycles, and the packaging signals (TRs). For propagation in *E. coli*, the genome contains a F-factor replicon. Enhanced GFP has been inserted as a marker gene and the hygromycin resistance gene allows for selection in eukaryotic cells. The cloning strategy has been described previously in more details (Hettich et al., 2006; Delecluse et al., 1998; Delecluse et al., 1999). The 293-VII+ helper genome represents one embodiment of the modified EBV genome detailed in this specification.

Figure 2:
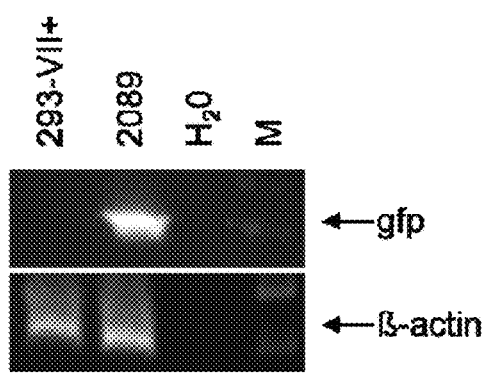

FIG. 2: The generated virus particles, termed VII+ VLP, (corresponding to the particle described in this specification) are free of detectable amounts of EBV-DNA. Particles released from induced VII+ packaging cell lines were isolated from the supernatant as described and analysed by PCR for the presence of viral DNA. In parallel, virus particles were isolated from induced 2089 cells, which release infectious virions upon induction of the productive phase. No EBV-DNA was detectable in VII+ VLPs. In contrast to 2089-particles. Viral DNAs that both carry the gene for enhanced GFP, were detected with a gfp-specific primers.

Figure 3A:
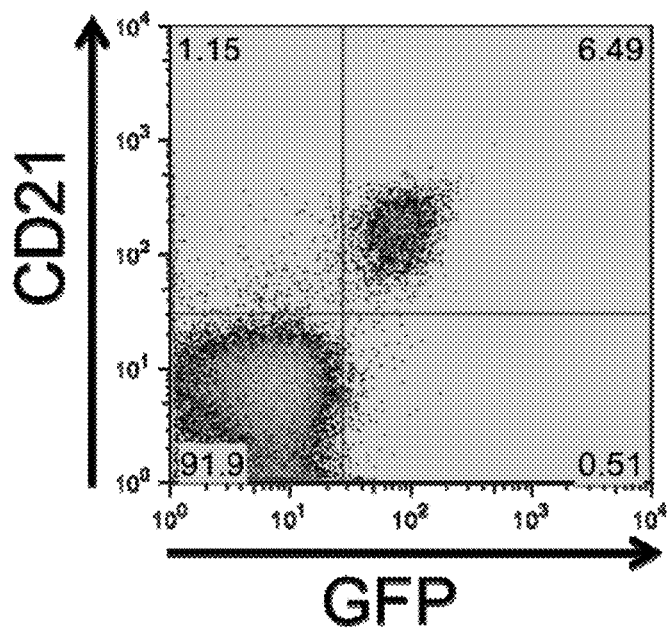

FIG. 3A: VII+ VLPs bind exclusively to CD21+ cells. In order to test the B-cell tropism of VII+ VLPs, PBMCS from a healthy donor were incubated with VII+ VLPs overnight. Binding of VII+ VLPs, as revealed by the transfer of GFP, was exclusively detectable on CD21+ cells.

Figure 3B:
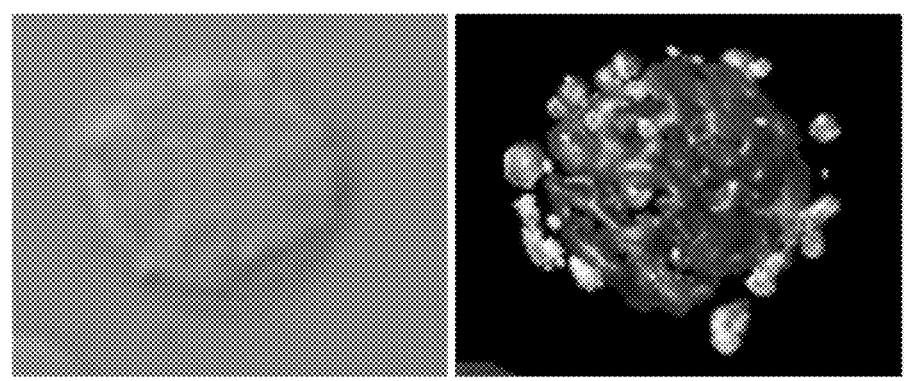

FIG. 3B: VII+ VLP's bind exclusively to CD21+ cells. In order to investigate the interaction of VLPs with B-cells in more detail, we performed confocal microscopy on VLP-incubated PBMCs that clearly revealed a co-localization of gp350, present in VII+ VLPs, and CD21 on the cell surface, indicative for a frank interaction of these two molecules.

Figure 4:
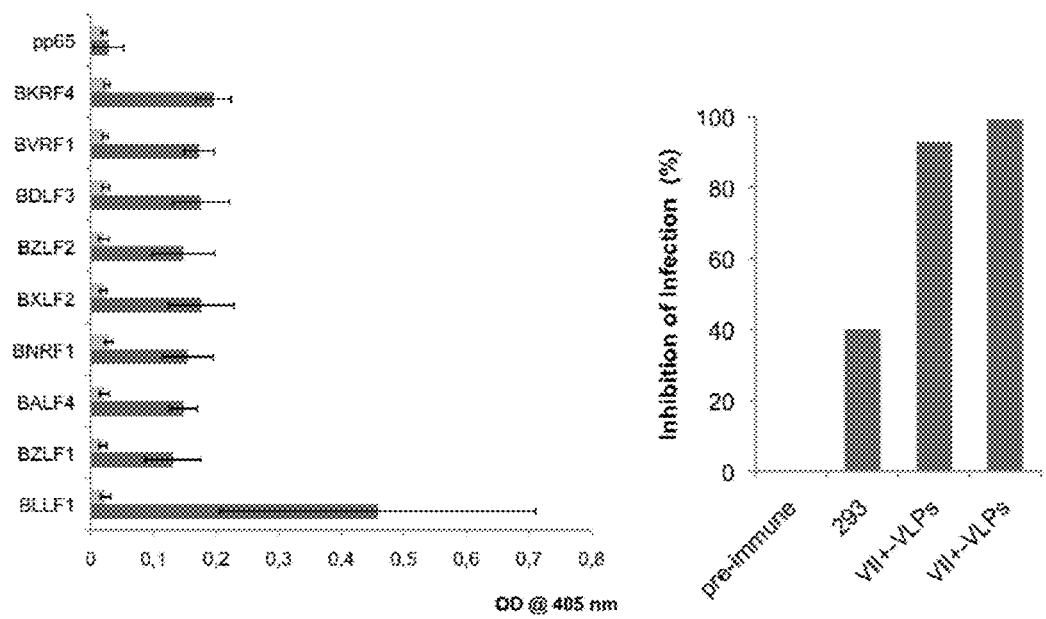

FIG. 4: VII+ VLPs induce neutralizing antibodies in naïve mice. BALB/c mice (n=4) were immunized twice with 10 μg VII+-VLPs (dark grey bars) or with the same amounts of 293 exosomes (n=2) (light grey bars). The blood was isolated 4 weeks after the second immunization and analysed for EBV-specific antibodies. (left) Mice immunized with VII+-VLPs but not those immunized with 293 exosomes had high levels of antibodies specific for various EBV proteins. 293 cells were transfected with an expression plasmid for the viral protein of interest and lysed one day later. A 96-well plate was then coated with the different lysates, washed and incubated with mouse sera at a dilution of 1:200. Presence of bound antibodies was detected with a peroxidase-conjugated anti-mouse-IgG antibody. 293 cells transfected with an expression plasmid for the CMV protein pp65 was used as a control. (right) The induced EBV-specific antibodies are neutralizing and inhibit infection of primary B-cells. Recombinant infectious EBV-particles (EBV-2089) were pre-incubated for 30 min with sera from mice immunized with either VII+-VLPs (n=2) or 293 exosomes (n=1) and were then used to infect human primary B-cells at a MOI of 0.1. 48 hours later, the number of infected cells, as revealed by GFP expression, were measured by flow cytometry. It became clear that 293 particles alone have a small inhibiting effect which is probably due to the induction of 293-specific antibodies and EBV-2089 is also 293-derived. However, inhibition by sera of VII+ VLP-immunized mice was significantly stronger and blocked infection almost completely.

Figure 5:
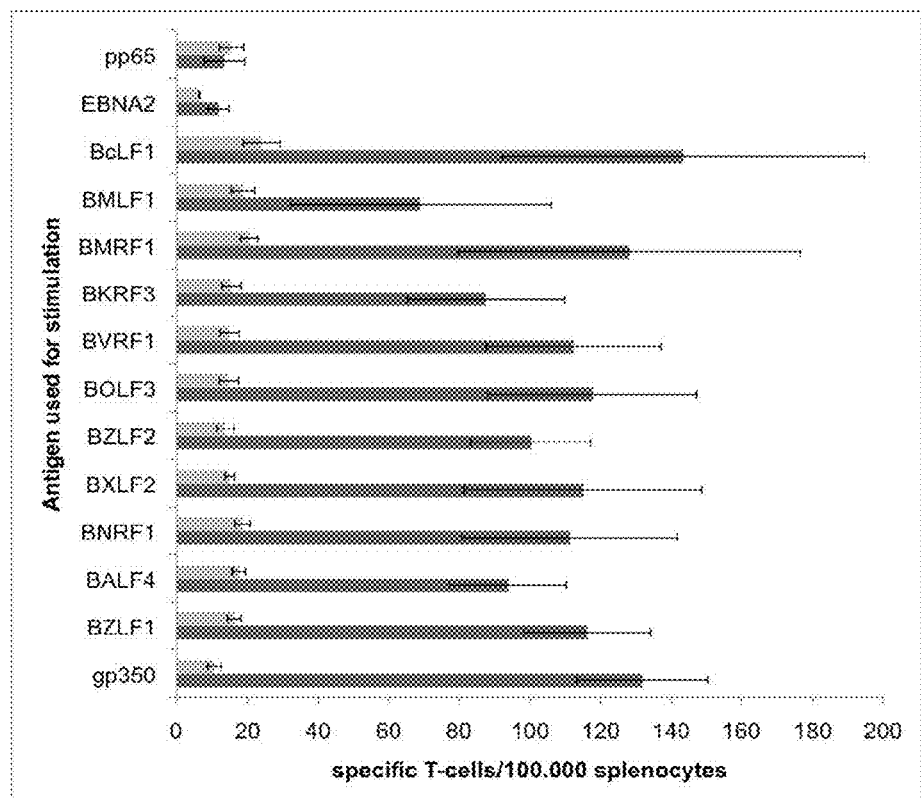

FIG. 5: VII+ VLPs. Induce the generation of EBV-specific Immuncompetent BALB/c mice were immunized twice with VII+-VLPs (10 μg, i.p.). and the spleens were isolated and analyzed 4 weeks after the second immunization. The presence of EBV-specific T-cells was measured in an mouse-specific Interferon-gamma ELISPOT using irradiated splenocytes that have been loaded with lysates from 293 cells, transiently transfected with expression plasmids for either of the EBV-proteins indicated. This Elispot revealed specific cellular immune responses against EBV polypeptides all of which have been described as contained in wild-type EBV (Johannsen et al, 2004). In contrast, no immune responses were detectable against EBNA2 and pp65, a polypeptide derived from cytomegalovirus, demonstrating the specificity of the assay.

Figure 6:
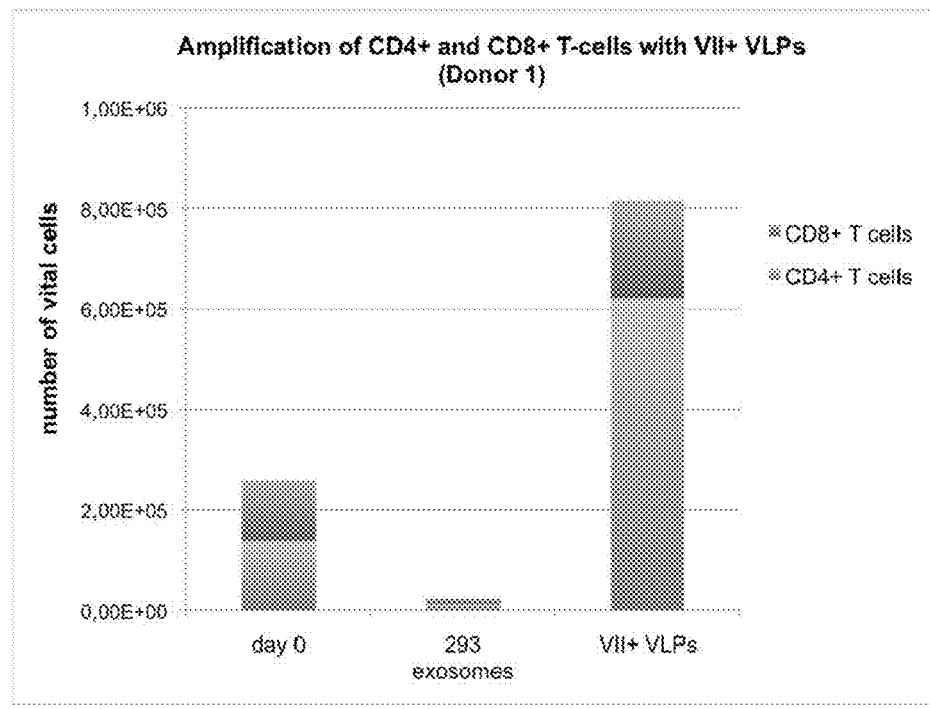
Figure 6:
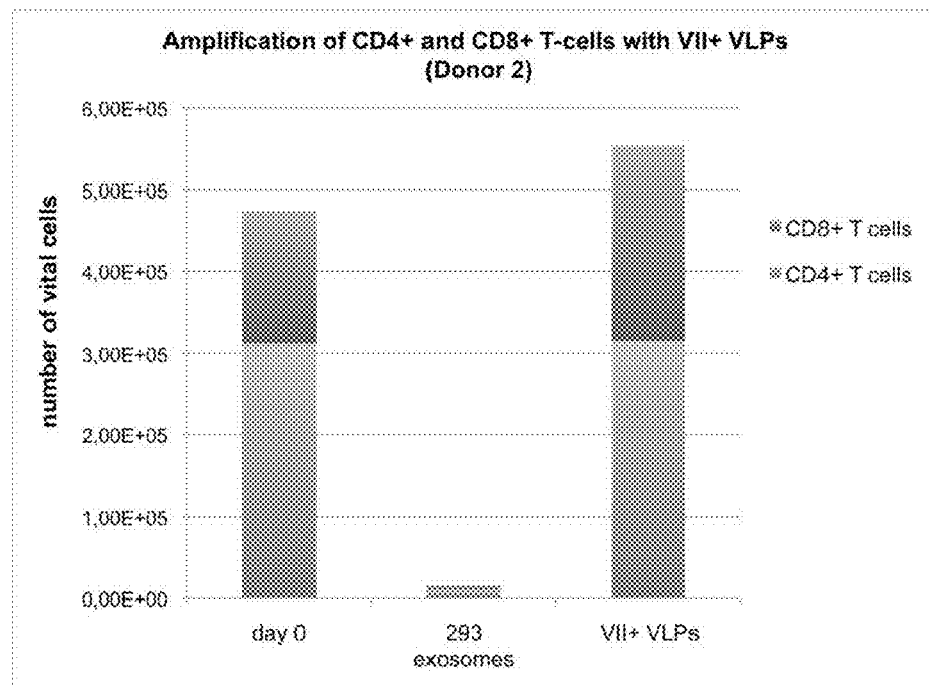

FIG. 6: Reactivation of CD4+ and CD8+ T-cells from EBV-positive donors. PBMCs from two donors were stimulated three times within eight days with VII+ VLPs 293-exosomes that do not contain any EBV-derived protein. Cells were counted and analysed by flow cytometry 12 days after the first stimulation.

Figure 7:
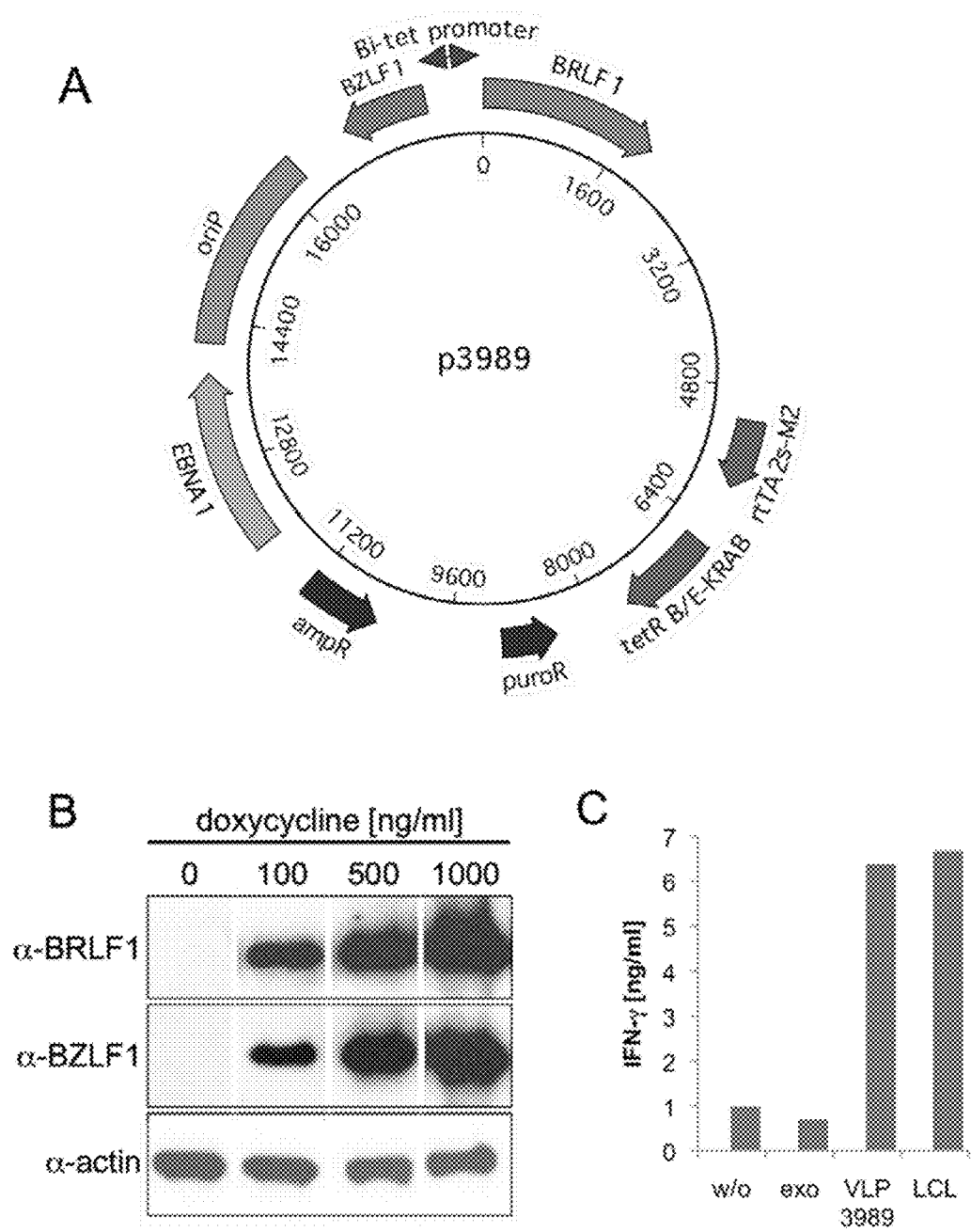

FIG. 7: Conditional activation of EBV's lytic phase in 293-VII+ cells. A derivative of the 293-VII+ cell line allows the continuous production of VLPs. (A) Plasmid map of the plasmid p3939, which was introduced into the 293-VII+ cell line. This expression plasmid contains the immediate early switch genes of EBV's lytic cycle. BZLF1 and BRLF1, under the control or a tetracycline-inducible bi-directional promoter together with regulatory genes (terR B/E-KRAB and rtTA2s-M2), the plasmid origin of DNA replication, oriP, and its transactivator EBNA1 (Bornkamm et al., 2005). p3989 is based on a previously described principle (Urlinger et al., 2000; Forster et al., 1999). Tetracyclinedependent expression of EBV's lytic phase activator proteins BZLF1 and BRLF1 is achieved from a tetracycline-regulated bidirectional promoter. This conditional expression system relies on the constitutive expression of a bicistronic expression cassette that encodes the tetracycline-controlled transactivator, rtTA2S-M2, and the Tat repressor-KRAB fusion protein (tTS-KRAB). The bidirectional promoter driving the genes of interest is downregulated through the tTS-KRAB repressor in the absence of doxycycline but induced upon its addition by the rtTA2S-M2 activator. (B) Western blot analysis indicated the induced expression of BZLF1 and BRLF1 in 293-VII+ cells with p3989 twelve hours upon addition of doxycycline. (C) PBMCs from an EBV-seropositive donor were loaded with VLPs from doxycycline induced 293-VII+-p3989 cells and used as stimulators for a gp350-specific CD4+ T cell clone. IFN-g release indicated that VLPs generated from 293-VII+ and 293-VII+-p3909 cells were comparable. Unloaded PBMCs (w/o) or PBMCs loaded with exosomes from HEK293 cells (exo) served as negative controls, an autologous LCL was the positive control.

Figure 8:
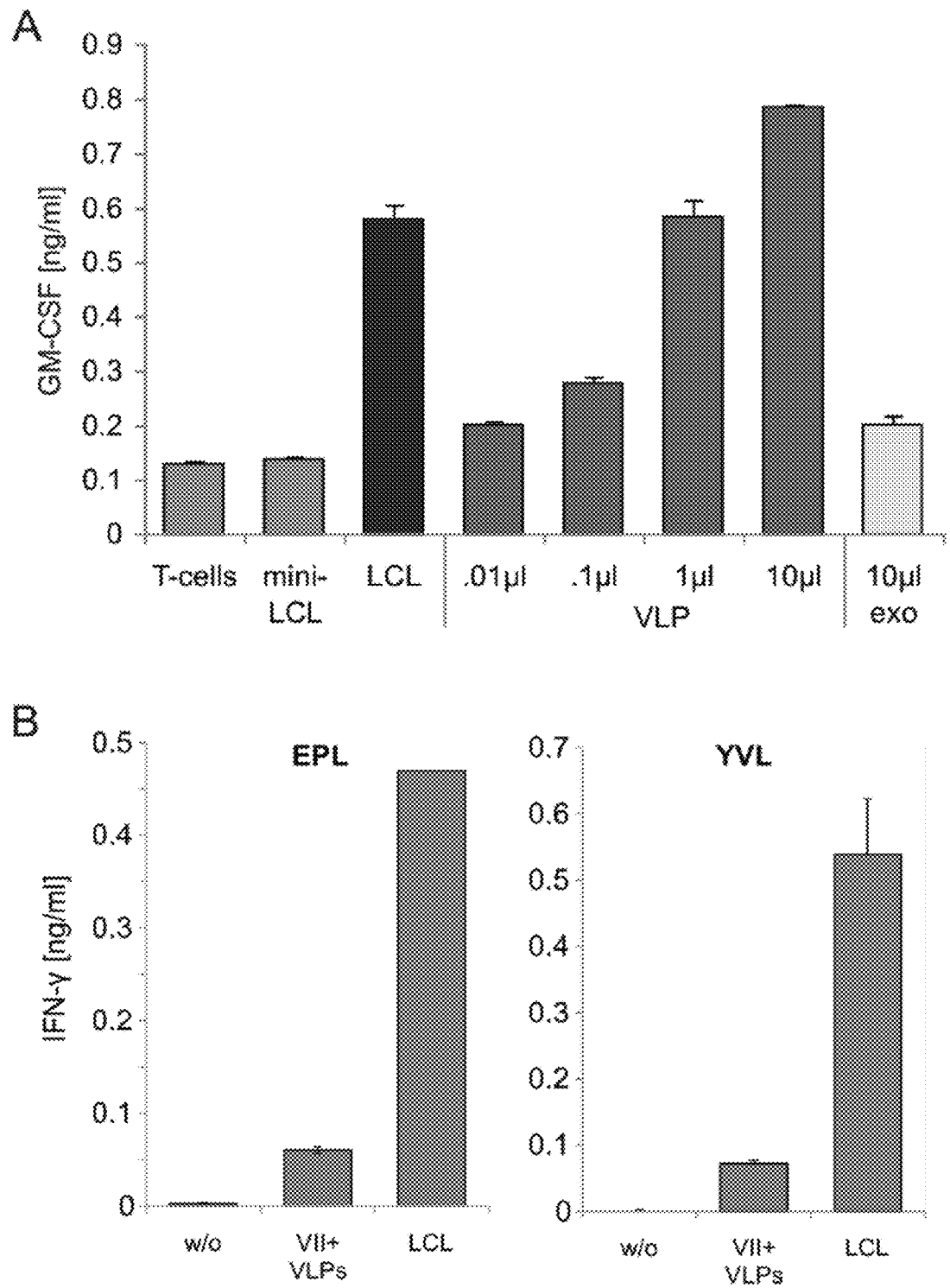

FIG. 8: VLP-loaded B cells efficiently reactivate an EBV-specific CD4+ and CD8+ T cell clone: (A) VLP-loaded B cells are potent stimulators of a BNRF1-specific CD4+ T cell clone. A mini-LCL line (Moosmann et al., 2002) was loaded with serial dilutions of VLPs obtained from lytically induced 293-VII+ cells. The loaded cells were used as stimulators for an autologous CD4+ T cell clone, which recognizes a BNRF I-specific epitope (Mautner et al., 2004). Stimulation of the T cell clone with the mini-LCL line loaded with exosomes (exo) from HEK293 cells was used as a negative control and an autologous LCL, which expresses BNRF1 was used as a positive control. (B) PBMCs from a HLA-A2+/B35+ donor were incubated with VLPs from 293-VII+ cells overnight or left untreated and were then used as stimulators for HLA-matched CD8+ T-cell clones specific for the EBV proteins BZLF1 (EPL, (Green et al., 2004)) and BRLF1 (YVL; (Saulquin et al., 2000)). An IFN-γ ELISA revealed a weak but distinct activation of T cells incubated with VLP-treated PBMCs but not with untreated PBMCs.

Figure 9:
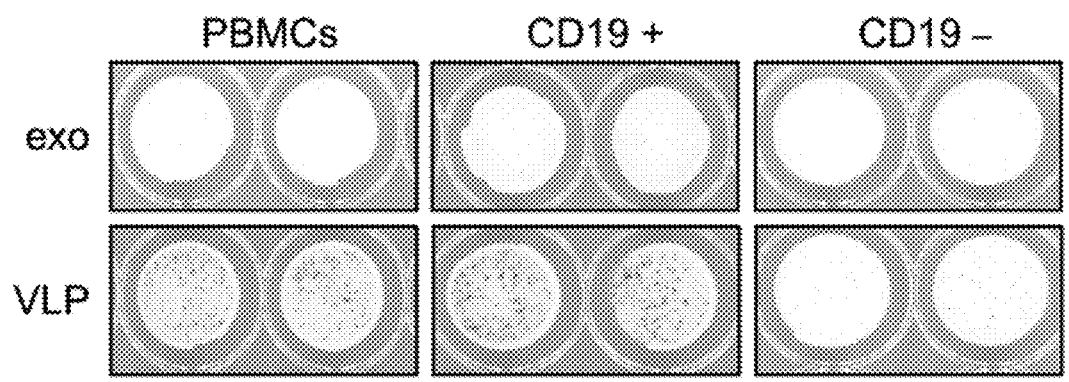

FIG. 9: Reactivation of EBV-specific T-lymphocytes with VLPs depends on CD19+ B cells. CD3+ T-cells from a healthy donor were stimulated three times within a period of 14 days with autologous, lethally irradiated stimulator cells as indicated, which had been preincubated with exosomes (exo) or VLPs from HEK293 cells or 293-VII+ cells overnight. The stimulator cells were either unfractionated PBMCs MACS-sorted CD19+ B cells or PBMCs from which the B cells were depleted (CD19−). After three rounds of stimulation, reactivation of EBV-specific T cells was assessed in an IFN-γ Elispot assay, using autologous PBMCs loaded with VLPs or exosomes as target. T cell reactivation was strictly dependent on the presence of CD19+ B cells as stimulators.

Figure 10:
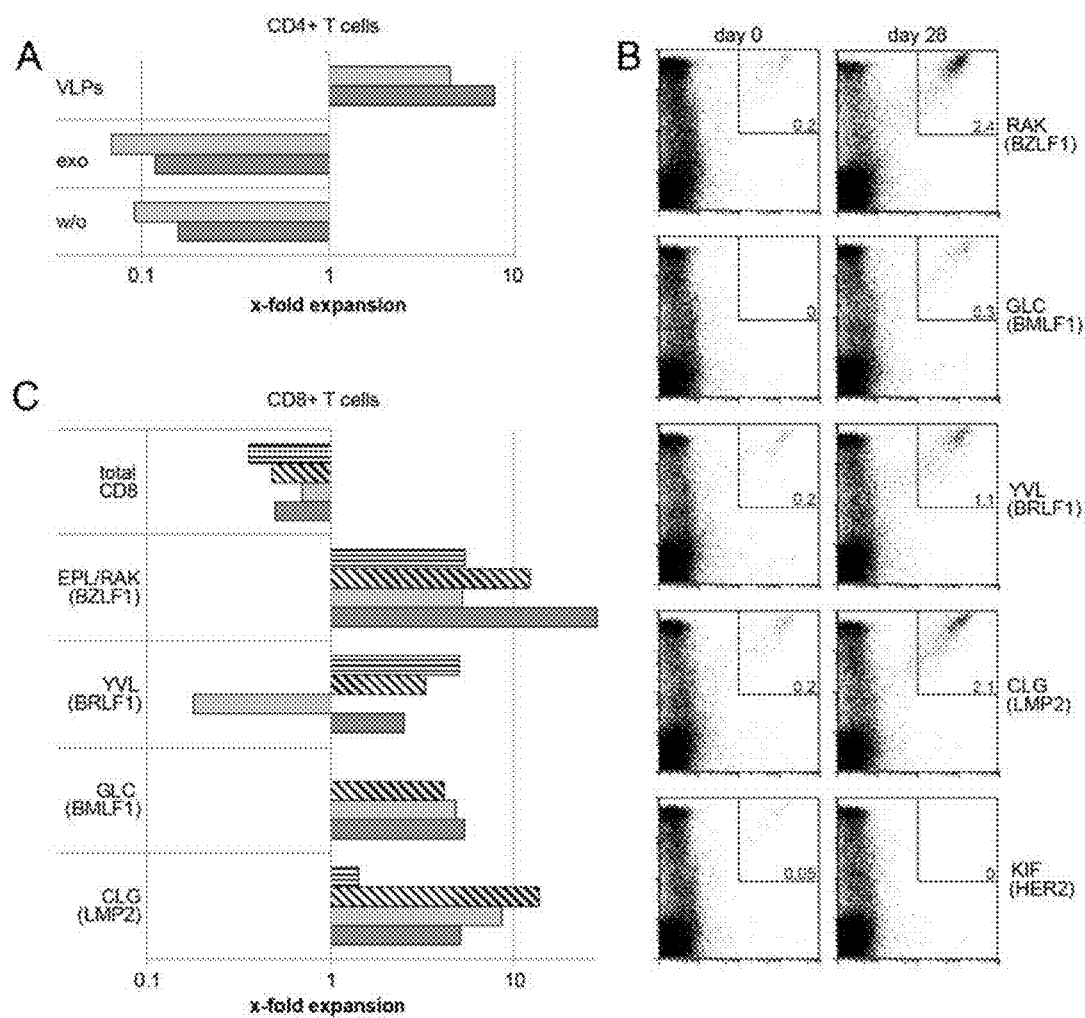

FIG. 10: VLPs from 293-VII+ cells selectively expand EBV-specific CD4+ and CD8+ T cells. PBMCs from different EBV-positive donors were lethally irradiated, loaded with either VLPs from lytically induced 293-VII+ cells, exosomes from HEK293 cells or were left untreated and used as stimulators for autologous PBMCs. After 28 days and three rounds of stimulation, cells were analyzed by FACS. (A) VLP- but not exosome-loaded (exo) or untreated (w/o) irradiated PBMCs expanded CD4+ cells as described recently (Adhikary et al., 2008). (B) PBMCs loaded with VLPs reactivated and expanded EBV-specific CD8+ T cells as revealed by staining with HLA B03/B08- or A02-restricted tetramers/pentamers to selected EBV protein epitopes. A tetramer (Kip to the cellular protein Her2/neu served as negative control. (C) VLP-loaded irradiated PBMCs reliably expanded EBV specific CD8+ cells from four different donors up to 15-fold within 28 days whereas the total number of CD8+ T cells dropped by about half compared to the initial CD8+ T cell numbers FIG. 11: VLPs elicit EBV-specific humoral and cellular immune responses in immunized mice. BALB/c mice were immunized twice with 10 μg VLPs from 293-VII+ cells (n=4) or with the same amounts of exosomes from HEK293 cells (n=2). Sera and splenocytes were analyzed four weeks after the last immunization. (A) In ELISAs sera from VLP-(black bars) but not from exosome immunized mice (grey bars) contain antibodies specific to EBV proteins present in virions. (B) Antibodies generated in mice immunized with VLPs from 293-VII+ cells neutralize infectious EBV. GFP-positive 2098 EBV stocks were pre-incubated for 30 min with sera from mice immunized with VLPs (VLP) or exosomes (exo) and subsequently used to infect human primary B cells at a calculated multiplicity of infection of 0.1. 48 hours later, the number of GFP-expressing infected cells was determined by flow cytometry. The neutralizing anti-gp350 antibody 72A1 was used as a positive control at two different concentrations. (C) VLPs from 293-VII+ cells activate EBV-specific T cells. The occurrence of EBV-specific T cells in mice immunized with VLPs (black bars) or exosomes (grey bars) was measured in a mouse-specific IFN-γ ELISPOT with irradiated splenocytes as antigen-presenting cells loaded with lysates from HEK293 cells, which had been transiently transfected with expression plasmids encoding the indicated viral proteins.

The examples illustrate the invention:

EXAMPLE 1: 293-VII+ CELLS RELEASE VLPS UPON INDUCTION THAT LACK VIRAL DNA BUT CONTAIN VARIOUS EBV PROTEINS

The inventors recently described the construction of two helper cell lines for the encapsidation of EBV-derived vectors into recombinant virus particles (Delecluse et al., 1999; Hettich et al., 2006). These cell lines harbor EBV helper genomes that lack the terminal repeats (TRs), the viruses packaging signals but instead contain genes for gfp. Consequently, these helper genomes cannot be encapsidated into viral particles but deliver in trans all proteins necessary for the packaging of suitable viral vectors and the assembly and release of recombinant and infectious EBV particles. The first generation cell line, TR-2, harbored an otherwise intact EBV genome which retained full transformation capacity for primary human B-cells (Delecluse et al., 1999.). In order to cope with rare illegitimate encapsidation of the helper genome and accidental recombination between viral vectors and the helper genome resulting in the release of recombinant virus particles with transformation capacity, the inventors later designed a second-generation packaging cell line, 293-VII+, with an EVB helper genome lacking roost of the viral genes essential for B-cell transformation (FIG. 1) (Hettich et al., 2006).

Surprisingly, the recombinant viral particles released from these helper cell lines maintain properties of wild-type EBV: they display a B-cell tropism and transducing capacity for both normal and malignant B-lymphocytes. Probably owed to its overexpression from the helper genome, these particles also contain the GFP protein so that their interaction with target cells can be monitored easily. Interestingly, the inventors observed that upon induction of the lytic cycle with a BZLF1 expression plasmid, p509 (Hammerschmidt and Sugden, 1988), the 293-VII+ cells released large amounts of GFP-positive particles into the supernatant even when a packable viral vector had not been co-transfected. Since many cell types and permanent cell lines constitutively release microvesicles termed exosomes and many viruses exploit the exosome biogenesis for their own assembly and egress (Calistri et al., 2009; Mori et al., 2008; Pelchen-Matthews et al., 2004), it was asked whether the particles released from 293-VII+ cells upon induction of the productive cycle, are exosome-like particles containing viral proteins.

The inventors therefore analyzed the composition and the properties of these particles in more detail. First, they checked by PCR, whether VLPs from VII+ cells contain viral DNA. For this, they induced EBV's Lytic phase in VII+ cells with p509 and, as a positive control, also in 2089 cells that harbor a TR+ EBV genome and release infectious virus particles (Delecluse et al., 1998). Three days later the supernatants were harvested from these cell hoes and precipated the released particles by ultracentrifugation. A PCR analysis of these particles revealed that EBV-DNA could be easily detected in 2089 particle but not in VLPs from VII+ cells (FIG. 2).

EXAMPLE 2: 293-VII+-VLPS HAVE AN EBV-LIKE B-CELL TROPISM

One of the proteins found to he incorporated into VLPs was gp350/220, the major viral envelope protein that mediates binding of the virion to human B-lymphocytes by interacting with CD21. The inventors, therefore, wanted to elucidate whether VLPs have a B-cell tropism similar to wildtype EBV. To do so, they incubated freshly isolated PBMCs overnight with concentrated VII+ VLPs and analysed binding of VLPs by FACS. For these experiments they took advantage of the fact that the enhanced GFP, expressed from the VII+ helper genome, is also incorporated into VLPs. As demonstrated in FIG. 3a, binding of VLPs is restricted to CD21+ cells, most probably B-cells, as judged by the fact the only CD21+ cells become GFP-positive. In contrast, binding of VLPs to CD21-negative cells could not be observed. In order to investigate the interaction of VLPs with B-cells in more detail, the inventors performed confocal microscopy on VLP-incubated PBMCs that clearly revealed a co-localization of gp350, present in VLPs, and CD21 on the cell surface, indicative for a frank interaction of these two molecules (FIG. 3b).

It has been described recently that VLPs derived from 293/TR− can efficiently reactive EBV-specific CD4+ T-cells upon engulfment by human PBMCs (Adhikary et al., 2008), it was sought to determine whether this holds also true for VII+-VLPs. To address this question, the inventors loaded irradiated primary PBMCs from a healthy donor with VII+-VLPs and then co-cultivated them with either autologous CD4+ T-cell clones specific for the EBV structural proteins BLLF1 and BNRF1 or with autologous PBMCs. These experiments demonstrated that VII+-VLP-loaded PBMCs efficiently reactivated specific CD4+ T-cell clones and autologous bulk T-cells as measured with an IFN-γ ELISA assay.

EXAMPLE 3: VII+-VLPS INDUCE NEUTRALIZING EBV-SPECIFIC ANTIBODIES IN NAÏVE HOSTS

The results from the previous sections demonstrated the potential of VLPs to stimulate EBV-specific recall immune responses. In a next series of experiments the inventors thus evaluated whether VLPs can also induce EBV-specific immune responses in naïve hosts in vivo, which is of course a prerequisite for prophylactic vaccines. To that purpose, the inventors intraperitoneally vaccinated BALB/c mice twice within a period of 14 days with 10 µg VLPs (n=4 whereas control mice (n=2) were immunized with the same amount of exosomes isolated from 293 supernatants. 4 weeks after the second immunization, the sera were collected and analyzed for the presence of EBV-specific antibodies and splenocytes were tested for EBV specificity. For this, the inventors coated 96-well cluster plates with a series of lysates from HEK293 cells which had been transiently transfected with expression plasmids for various EBV proteins.

As shown in FIG. 4, sera from VII+-VLP-immunized mice but not from 293-exosomes-immunized mice revealed strong immunoreactivity and thus the induction of antibodies specific for various EBV-proteins which have recently been identified as components of EBV particles (Johannsen et al. 2004). All antibodies were unambiguously detectable in sera from VLP-immunized mice at 1,200 (FIG. 4) and 1:1.000 dilutions (not shown). Of interest, the inventors also detected antibodies to the transcription factor BZLF-1, which, as mentioned above, is present at high levels in VLP-releasing VII+ cells and is incorporated into VII+ VLPs. In contrast, mice immunized with 293 exosomes revealed no detectable levels of EBV-specific antibodies. As a control, the inventors measured the reactivities of the sera against lysates from 293 cells transfected with expression plasmids encoding the major tegument protein of CMV, pp65, and the EBV transactivator, EBNA2. This protein is translated from the open reading frame BYRF1, which has been deleted from the VII+ helper genome (see FIG. 1). The inventors were not able to detect any reactivity against these two proteins, indicative for the specificity of these assays. Of interest, significant antibody titers in VLP-injected mice were already detectable seven days after the first immunization, indicative for the high immunogenicity of VII+-VLPs (data not shown).

To test whether the EBV-specific antibodies are neutralizing, the inventors quantified to what extent they inhibit the infection of primary B-cells by EBV. For this, they made use of an recombinant EBV (2089) carrying the gfp gene that is expressed in infected cells. (Delecluse et al., 1998). Primary B-cells isolated from fresh adenoids were infected with EBV-2089, pre-incubated with mouse sera for 30 min, at an MOI of 0.1 and the number of infected cells was quantified 48 hours later by FACS analysis. As shown in FIG. 4, sera from VLP-infected mice inhibited infection of primary human B-cells with EBV. As can be seen, also sera from 293-immunized mice have a weak inhibitory effect that is probably due to 293-specific antibodies recognizing 293-derived EBV-2089.

EXAMPLE 4: VLPS INDUCE EBV-SPECIFIC CELLULAR IMMUNE RESPONSES

The inventors next asked whether the immunization of naïve mice with VLPs also induced EBV-specific cellular immune responses, which are known to be essential for immune surveillance of the virus and of EBV-infected cells (Hislop et al., 2007). Therefore, they isolated the spleens of VLP-immunized mice and generated a single-cell suspension. We incubated $2 \times 10^5$ splenocytes over night with lysates from 293 cells that had been transiently transfected with expression plasmid for either of those EBV proteins which have also been used for the detection of EBV-specific antibodies to allow for engulfment, proteolytic degradation and presentation of VLP-derived proteins. Activation of T-cells was measured 24 hours later by an Interferon-gamma Elispot.

EXAMPLE 5: INTRODUCING A $3^{RD}$ GENERATION PACKAGING CELL LINE

TR-2 and 293-VII+ are two packaging cell lines in which EBV's productive life cycle is induced by transient transfection of an expression plasmid encoding BZLF1, which is sufficient to initiate the switch from the latent to the lytic cycle. However, large scale production of clinical grade VLPs depends on a cell line that permanently releases.

To overcome these restrictions and to move the first steps towards a standardized and more constant production of VLPs. The inventors designed a new packaging cell line, termed iVII+ that, in addition to the VII+ helper genome, stably carries a second plasmid encoding an inducible BZLF1 and, in addition, BRLF1, which is another viral immediate early protein that, in cooperation with BZLF1, induces the lytic cycle in epithelial cells (Zalani et al., 1996). When cultured in the presence of doxycyclin, iVII cells maintain the lytic cycle and release VLPs constitutively without any detectable changes in cell phenotype.

EXAMPLE 6: RE-ACTIVATION OF EBV-SPECIFIC CELLS

In order to define whether VLPs obtained from 293-VII+ cells are engulfed by human 8 cells and have the potential to re-activate EBV-Specific T cells, a lymphoblastoid B cell line (LCL) transformed with a mini-EBV (Kempkes et al., 1995) was incubated with VLPs from 293-VII+ cells. Then the loaded LCL were co-cultivated with an autologous CD4+ T cell clone specific for the EBV tegument protein BNRF1 not encoded in mini-EBVs (Kempkes et al., 1995). The experiments demonstrated that VLP-loaded B cells efficiently reactivated the CD4+ T cell clone as measured by a GM-CSF ELISA assay (FIG. 8A). This set of experiments shows that VLPs from 293-VII+ cells specifically interact with, and are engulfed by, human B cells, which, in turn, are potent antigen presenting cells and stimulators of EBV-specific CD4+ T cells corroborating the findings of Adhikary et al., 2008.

EXAMPLE 7: VLPS RE-ACTIVATE CD8+ T CELLS FROM SEROPOSITIVE HOSTS

The efficacy of vaccines depends on the generation of a long lasting immunological memory, which relies on both CD4+ and CD8+ T cells. It was to be determined whether VLPs of 293-VII+ cells can activate EBV-specific CD8+ T cells, a cell population that is mandatory for surveillance of EBV-infected cells in vive. To test the capacity of VLPs to reactive CD8+ memory T cells, PBMCs were first incubated with VLPs from 293-VII+ cells or exosomes from 293 cells overnight and then were used as targets for EBV-specific CD8+ T-cell clones. An IFN-γ ELISA revealed a weak but distinct activation of T cells that were incubated with PBMCs that were pre-incubated with VLPs (FIG. 8B). In the next series of experiments PBMCs from EBV-seropositive donors were stimulated with autologous, irradiated PBMCs pre-incubated with VLPs from 293-VII+ cells. After 28 days and three rounds of stimulation a detailed flow cytometric analysis revealed that PBMCs loaded with VLPs from 293-VII+ cells induced the proliferation of autologous CD4+ T cells in contrast to PBMCs loaded with exosomes from parental HEK293 cells or untreated PBMCs (FIG. 10A). In order to determine whether VLPs also reactivated EBV-specific CD8+ T cells their initial frequency in donor PBMCs was measured and compared to in vitro VLP-expanded CD8+ T cell populations for the specific recognition of known HLA class I-restricted EBV epitopes, which elicit strong CD8+ T cell immune responses in infected hosts. The peptide epitope CLG of the latent protein LMP2 and the peptide epitopes EPL/RAK, GLC and YVL of the early lytic proteins BZLF1, BMLF1 and BRLF1, respectively, were chosen which are HLA B03/B08 or A02 restricted. Staining with HLA/peptide pentamers revealed a small but detectable fraction of CD8+ T cells in the initial donor PBMCs predominantly recognizing the early lytic epitopes (FIG. 10B). The fraction of epitope-specific CD8+ T cells expanded from about 0.15% to 0.25% to 1.1% to 2.4% in three rounds of VLP stimulation (FIG. 10B) and absolute numbers of epitope-specific CD8+ T cells increased up to 10-fold approximately (FIG. 10C). This finding is in conflict with a recent publication because B cells did not efficiently process viral particles or VLPs for HLA class I-associated cross-presentation in contrast to professional antigen presenting cells such as dendritic cells or macrophages (Keller et al., 2009). Therefore it was expected that monocytes or macrophages in PBMCs might present VLP-derived peptides to CD8+ T cells for their activation. To address this controversy, CD19+ and CD19− cells were purified from PBMCs and incubated the fractionated mononuclear cells with VLPs from 293-VII+ cells or exosomes from HEK293 cells. Reactivation of T cells immediately after the third round of stimulation with VLP-loaded PBMCs was quantified in IFN-γ Elispot assays with CD19+ and CD19− PBMCs. The results clearly indicated that only CD19+ B cells are potent presenters of VLP-derived viral antigens (FIG. 9). Hardly any T cells were identified with CD19− PBMCs as antigen presenting cells (FIG. 9) suggesting that only B cells activated the virus epitope-specific cells including HLA class I restricted C08+ T cells.

EXAMPLE 8: VLPS ELICIT EBV-SPECIFIC HIGH-TITER NEUTRALIZING ANTIBODIES AND CELLULAR IMMUNE RESPONSES IN NAÏVE BALB/C MICE

Figure 11:
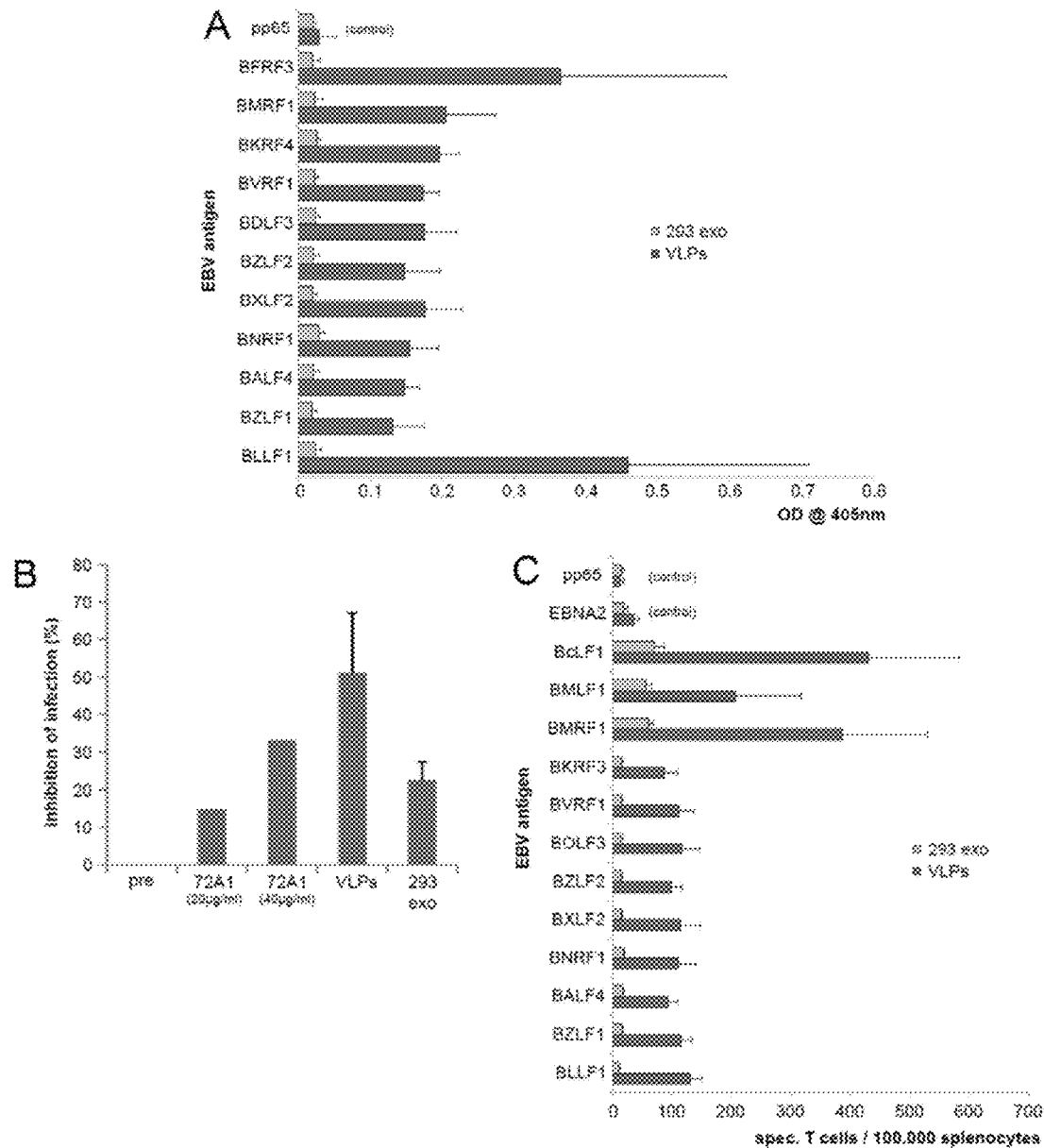

This is a repetition of example 3 (see also FIG. 4) including further data (see. FIG. 11). For the sake of completeness, the methodology is described again as it includes variations. The inventors immunized BALB/c mice (four animals) twice within a period of 14 days with 10 µg VLPs whereas control mice (two animals) were immunized with the same amount of exosomes from HEK293 cells. Four weeks after the second immunization, the sera were analyzed for the presence of EBV-specific antibodies with an ELISA and protein lysates from HEK293 cells as antigens, which had been transiently transfected with expression plasmids for single EBV proteins as shown in FIG. 11A. To avoid background signals caused by antibodies raised against HEK293-derived proteins, sera were pre-incubated for 2 hours with HEK293 lysates coated to cell culture plates. As shown, sera from VLP-immunized mice but not mice immunized with exosomes from HEK293 cells revealed strong immunoreactivity against the selected viral proteins, which are components of virions of EBV. All antibodies were unambiguously detectable in sera from VLP-immunized mice at 1 to 200 dilutions (FIG. 11A). VLP-immunized mice also developed high levels of antibodies against the transcription factor Zta, encoded by the BZLF1 gene. As controls, the reactivity of the sera against lysates from HEK293 cells transfected with expression plasmids encoding CMV tegument protein pp65 and the EBV transactivator EBNA2 was measured. EBNA2 is translated from the BYRF1 gene, which is deleted in the EBV helper genome in 293-VII+ cells (FIG. 1). As anticipated, no humoral responses against these two proteins in the VLP-immunized mice was detected indicating the specificity of these assays.

To learn whether sera from VLP-immunized animals contained EBV-specific neutralizing antibodies, which can inhibit cellular infection with EBV, the recombinant gfp encoding 2089 EBV, which confers GFP fluorescence to B cells as a quantitative measure of infection (Delecluse et al., 1998) was used. Virus stocks of 2089 EBV were pre-incubated with mouse sera for 30 min and then used to infect primary human B cells at a calculated multiplicity of infection of 0.1. After 48 hours GFP-positive infected cells were quantified by flow cytometry. As shown in FIG. 11B, sera from VLP-immunized mice impaired infection with EBV but sera from mice immunized with exosomes from HEK293 cells also had an inhibitory but weaker effect probably due to the induction of antibodies against 293-derived proteins. Virus stocks of 2089 EBV are obtained from HEK293 producer cells (Delecluse et al., 1998) suggesting that sera from mice immunized with exosomes from HEK293 cells could also recognize 2089 EBV particles and compromise their infectivity.

Next, it was asked whether the immunization of mice led to the induction of EBV-specific cellular immune responses, which are essential for the immune surveillance of EBV. Single cells were prepared from spleens of VLP-immunized and control mice described above. Lethally irradiated splenocytes from individual mice were incubated with lysates obtained from HEK293 cells transiently transfected With single expression plasmids encoding the viral genes shown in FIG. 11C and present in virions. To allow for adsorption, proteolytic degradation and presentation of the exogenously added lysates, the splenocytes were incubated for five hours and subsequently washed to remove free lysate. The capacity of the cells to present antigen was assessed with 5×105 non-irradiated splenocytes, which were added as indicators. The activation of the indicator cells was determined in an IFN-γ Elispot assay after 24 hours. As shown in FIG. 11C, splenocytes from VLP-immunized mice but not from control mice immunized with exosomes from HEK293 cells were clearly reactivated. Taken together, this experiment indicated that VLPs from 293-VII+ cells can induce an EBV-specific cellular immune response in naïve mice.

LITERATURE

Adhikary, D., Behrends, R. Feederle, H. J. Delecluse, and J. Mautner. 2008. Standardized and highly efficient expansion of Epstein-Barr virus-specific CD4+ T cells by using virus-like particles. J. Virol. 82:3903-3911.

Becker, N., Fortuny, J., Alvaro, T., Nieters, A., Maynadie, M., Foretova, L., Staines, A., Brennan, P., Boffetta, P., Cocco, P. L., and de Sanjose, S. (2009). Medical history and risk of lymphoma: results of a European case-control study (EPILYMPH). J Cancer Res Clin Oncol 135, 1099-1107.

Braasch, D. A., and Corey, D. R. (2001). Locked nucleic acid (LNA): fine-tuning the recognition of DNA and RNA. Chem Biol 8, 1-7.

Bornkamm, G. W., C. Berens, C, Kuklik-Roos, J. M, Bechet, G. Laux, Bachl, M. Korndoerfer, M. Schlee, M. Holzel, A. Malamoussi, R. D. Chapman, F. Nimmerjahn, J. Mautner, W. Hillen, H. Bujard, and J. Feuillard. 2005. Stringent doxycycline-dependent control of gene activities using an episomal one-vector system, Nucleic Acids Res 33:e137

Busse, C., Feederle, R., Schnolzer, M., Behrends, U., Mautner, J., and Delecluse, H. J. (2010). Epstein-Barr viruses that express a CD21 antibody provide evidence that gp350's functions extend beyond B-cell surface binding: J Virol 84, 1139-1147.

Calistri, A., Salata, C., Parcilin, C., and Palu, G. (2009). Role of multivesicular bodies and their components in the egress of enveloped RNA viruses. Rev Med Virol 19, 31-45.

Chesnokova L. S., Nishimura, S. L. and Hutt-Fletcher, L. M. (2009). Fusion of epithelial cells by Epstein-Barr virus proteins is triggered by binding of viral glycoproteins gHgL to integrins alphavbeta6 or alphavbeta8. Proc Natl Acad Sci USA 106, 20464-20469.

Delecluse, H. J., Hilsendegen, T, Pich, D., Zeidler. R., and Hammerschmidt, W. (1998). Propagation and recovery of intact, infectious Epstein-Barr virus from prokaryotic to human cells. Proc Natl Acad Sci USA 95, 8245-8250.

Delecluse, H. J., Pith, D., Hilsendegen, T., Baum, C., and Hammerschmidt, W. (1999). A first-generation packaging cell line for Epstein-Barr virus-derived vectors Proc Natl Acad Sci USA 96, 5188-5193.

Duchini, A., Goss, J. A., Karpen, S., and Pockros. P. J. (2003). Vaccinations for adult solid-organ transplant recipients: current recommendations and protocols. Clin Microbial Rev 16, 357-364.

Elliott, S. L., Suhrbier, A., Miles, J. J., Lawrence, G., Pye, S. J., Le, T. T., Rosenstengel, A., Nguyen, T., Allworth, A, Burrows, S. R., Cox, J., Pye, D., Moss, D. J., and Bharadwaj, M. (2008). Phase I trial of a CD8+ T-cell peptide epitope-based vaccine for infectious mononucleosis, J Virol 82, 1448-1457.

Everly, M. J., Bloom, R. D., Tsai, D. E, and Trofe, J. (2007). Posttransplant lymphoproliferative disorder, Ann Pharmacother 41, 1850-1858.

Forster, K., V. Helbl, T. Lederer, S. Urlinger, N. Wittenburg, and W. Hillen. 1999. Tetracycline-inducible expression systems with reduced basal activity in mammalian cells. Nucleic Acids Res 27.708-710.

Gires, O., Zimber-Strobl, U., Gonnella, R., Ueffino, M., Marschall, G., Zeidler, R., Pich, D., and Hammerschmidt, W. (1997). Latent membrane protein 1 of Epstein-Barr virus mimics a constitutively active receptor molecule, EMBO J 16, 6131-6140.

Goldacre, M. J., Wotton, C. J., and Yeates, B. G. (2009). Associations between infectious mononucleosis and cancer: record-linkage studies, Epidemiol Infect 137, 672-680.

Green, K. J., J. J. Miles, J. Tellam, W. J. van Zuyien, G. Connolly, and S. P. Burrows. 2004. Potent T cell response to a class I-binding 13-mer viral epitope and the influence of HLA micropolymorphism in controlling epitope length. Eur J Immunol 34:2510-2519.

Gu, S. Y., Huang, T. M., Roan, L. Mica, Y, Lu, H., Chu, C. M., Motz, M., and Wolf, H. (1995). First EBV vaccine trial in humans using recombinant vaccinia virus expressing the major membrane antigen. Dev Biol Stand 84, 171-177.

Hettich, E., Janz, A., Zeidler, R., Pich, D., Hellebrand, E., Weissflog, B., Moosmann, A., and Hammerschmidt, W. (2006). Genetic design of an optimized packaging cell line for gene vectors transducing human B cells. Gene Ther 13, 844-856.

Hislop, A. D., Taylor, G. S., Sauce, D., and Rickinson, A. B. (2007). Cellular responses to viral infection in humans: lessons from Epstein-Barr virus. Annu Rev Immunol 25, 587-617.

Imashuku, S. (2007). Systemic type Epstein-Barr virus-related lymphoproliferative diseases in children and young adults: challenges for pediatric hemato-oncologists and infectious disease specialists. Pediatr Hematol Oncol 24, 563-568.

Janz, A., Dezel, M., Kurzeder, C., Mautner, J., Pion, D., Kost, M., Hammerschmidt, W., and Delecluse, H. J. (2000). Infectious Epstein-Barr virus lacking major glycoprotein BLLF1 (gp350/220) demonstrates the existence of additional viral ligands. J Virol 74, 10142-10152.

Johannsen. E., Luftig, M., Chase, M. R., Weicksel, S., Cahir-McFarland, E., Manes, D., Sarracino, D., and Kieff, E. (2004). Proteins of purified Epstein-Barr virus. Proc Natl Acad Sci USA 101, 16286-16291.

Keller, S. A., von Allmen C. E., Hinton, H. J., Bauer, M., Muntwiler, S., Dietmeler, K., Saudan, P., and Bachmann, M. F. (2009). Follicular and marginal zone B cells fail to cross-present MHC class I-restricted epitopes derived from viral particles. J Immunol 182, 6261-6266.

Kempkes, B., D. Pich, R. Zeidler, B. Sudden, and W. Hammerschmidt. 1995. Immortalization of human B lymphocytes by a plasmid containing 71 kilobase pairs of Epstein-Barr virus DNA. J. Virol. 69:231-238.

Kieff. E., and Rickinson, A. (2007). Epstein-Barr Virus and Its Replication. In Fields Virology, Knipe, D., and P. Humley, eds. (Philadelphia, Pa.: Lippincott Williams & Wilkins), pp. 2604-2654.

Lopes, V., Young, L. S., and Murray, P. G. (2003). Epstein-Barr virus-associated cancers; aetiology and treatment. Herpes 10, 78-82.

Lu, G., Xie, Z. D., Zhao, S. Y., Ye, L. J., Wu, R. H., Liu, C. Y., Yang, S., Jin, Y. K., and Shen, K. L. (2009). Clinical analysis and follow-up study of chronic active Epstein-Barr virus infection in 53 pediatric cases. Chin Med J (Engl) 122, 262-266.

Mautner, J., D. Pich, F. Nimmerjahn, S. Milosevic. D. Adhikary H. Christoph. K. Witter, G. W. Bornkamm, W. Hammerschmidt, and U. Behrends. 2004. Epstein-Barr virus nuclear antigen 1 evades direct immune recognition by CD4+ T helper Eur J Immunol 34:2500-2509.

Mendoza, F., Kunitake H., Laks, H., and Odim, J. (2006). Post-transplant lymphoproliferative disorder following pediatric heart transplantation. Pediatr Transplant 10, 60-66.

Moosmann, A., N. Khan, M. Cobboid, C. Zentz, H. J. Delecluse, G. Hollweck, A. D. Hislop, N. W. Blake, D. Croom-Carter, B. Wollenberg, P. A. Moss, R. Zeidler, A. B. Rickinson, and W. Hammerschmidt. 2002. B cells immortalized by a mini-Epstein-Barr virus encoding a foreign antigen efficiently reactivate specific cytotoxic T cells. Blood 100:1755-1764.

Mori, Y., Koike, M., Moriishi, E., Kawabata, A., Tang, H., Oyaizu, H., Uchiyama, Y., and Yamanishi, K. (2008). Human herpesvirus-6 induces MVB formation, and virus egress occurs by an exosomal release pathway. Traffic 9, 1728-1742.

Moutschen, M., Leonard, P., Sokal, E. M., Smets, F., Haumont, M., Mazzu, P., Bonen, A., Denamur, F., Peeters, P., Dubin, G., and Denis, M. (2007). Phase studies to evaluate safety and immunogenicity of a recombinant gp350 Epstein-Barr virus vaccine in healthy adults. Vaccine 25, 4697-4705.

Niedobitek, G. (1999). The Epstein-Barr virus: a group 1 carcinogen? Virchows Arch 435, 79-86.

Omerovic, J., Lev, L., and Longnecker, R. (2005). The amino terminus of Epstein-Barr virus glycoprotein gH is important for fusion with epithelial and B cells. J Virol 79, 12408-12415.

Pelchen-Matthews, A., Raposo, G., and Marsh, M. (2004). Endosomes, exosomes and Trojan viruses. Trends Microbiol 12, 310-316.

Pickering, L. K., Baker, C. J., Freed, G. L., Gall, S. A., Grogg, E., Poland, G. A., Rodewald, L. E., Schaffner, W., Stinchfield, P., Tan, L. Zimmerman, R. K., and Orenstein, W. A. (2009). Immunization programs for infants, children, adolescents, and adults: clinical practice guidelines by the infectious Diseases Society of America. Clin Infect Dis 49, 817-840.

Rees, L. Tizard, E. J., Moraan, A. J., Cubitt, W. D., Finerty, S., Oyewole-Eletu, T. A., Owen, K. Royed, C., Stevens, S. J., Shroff, R. C., Tanday, M. K., Wilson, A. D., Middeldorp, J. M., Amlot, P, L. and Steven, N. M. (2009). A phase I trial of epstein-barr virus gp350 vaccine for children with chronic kidney disease awaiting transplantation. Transplantation 867, 1025-1029.

Saulquin, X., C. Ibisch, M., A. Peyrat, E. Scotet, M. Hourmant, H. Vie, M. Bonneville, and E. Houssaint. 2000. A global appraisal of immunodominant CD8 T cell responses to Epstein-Barr Virus and cytomegalovirus by bulk screening. Eur J Immunol 30:2531-2539.

Silva, A. L. Omerovic, J., Jardetzky, T. S., and Longnecker, R. (2004). Mutational analyses of Epstein-Barr virus glycoprotein 42 reveal functional domains not involved in receptor binding but required for membrane fusion. J Virol 78, 5946-5956.

Sokal, E. M., Hoppenbrouwers, K., Vandermeulen, C., Moutschen, M., Leonard, P., Moreels, A., Haumont, M., Bolien, A., Smets, F., and Denis, M. (2007). Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. J Infect Dis 196, 1749-1753.

Sorem, J., and Longnecker, R. (2009). Cleavage of Epstein-Barr virus glycoprotein B is required for full function in cell-cell fusion with both epithelial and B cells, J Gen Virol 90, 591-595.

Succi, R. C., and Farhat, C. K. (2006). Vaccination in special situations. J Pediatr (Rio J) 82, S91-100.

Swerdlow, A. J., Higgins, C. D. Hunt. B. J., Thomas, J. A., Burke, M. M., Crawford, D. H., and Yacoub, M. H. (2000). Risk of lymphoid neoplasia after cardiothoracic transplantation. a cohort study of the relation to Epstein-Barr virus. Transplantation 69, 897-904.

Taylor, A. L., Marcus, R., and Bradley, J. A. (2005). Post-transplant lymphoproliferative disorders (PTLD) after solid organ transplantation. Crit Rev Oncol Hematol 56, 155-167.

Thacker, E. L., Mirzaei, F., and Ascherio, A. (2006). Infectious mononucleosis and risk for multiple sclerosis: a meta-analysis. Ann Neurol 59, 499-503.

Tobi, M. Morag, A., Ravid, Z., Chowers, I., Feldman-Weiss, V., Michaeli, Y., Ben-Chetrit, E., Shalit, M., and Knobler, H. (1982). Prolonged atypical illness associated with serological evidence of persistent Epstein-Barr virus infection. Lancet 1, 61-64, Urlinger, S., U. Baron, M. Theilmann, M. T. Hasan, H. Bujard, and W. Hillen. 2000. Exploring the sequence space for tetracycline-dependent transcriptional activators: novel mutations yield expanded range and sensitivity. Proc Natl Acad Sci USA 97:7963-7968.

Zaadstra, B. M., Chorus, A. M., van Buuren, S., Kalsbeek, H., and van Noort, J. M. (2008). Selective association of multiple sclerosis with infectious mononucleosis. Mult Scler 14, 307-313.

Zalani, S., Holley-Guthrie, B., and Kenney, S. (1996). Epstein-Barr viral latency is disrupted by the immediate-early BRLF1 protein through a cell-specific mechanism. Proc Natl Acad Sci USA 93, 9194-9199.

The invention claimed is:

1. A method for eliciting CD8+ T-cells specific for an EBV antigen in a subject, comprising administering to said subject an Epstein-Barr virus-like particle (VLP), thereby eliciting CD8+ T-cells specific for an EBV antigen;

wherein the VLP comprises at least one difference in comparison to a wildtype EBV genome lacking one or more sequences encoding EBV polypeptides that are required for B-cell transformation and/or comprising one or more sequences encoding EBV polypeptides whose B-cell transformation capacity is disabled, wherein the polypeptide whose transformation capacity is disabled is the LMP-1 polypeptide.

2. The method of claim 1, wherein the one or more EBV polypeptides required for B-cell transformation are selected from the group consisting of EBNA-2, EBNA-3a, EBNA-3b and EBNA-3c.

3. A method of generating an Epstein-Barr virus-like particle (VLP), the method comprising:

(a) transfecting a cell with a modified EBV genome, wherein said modified EBV genome in comparison to a wildtype EBV genome at least lacks one or more sequences that are required for the packaging of said wildtype EBV genome, and/or comprises one or more sequences encoding EBV polypeptides whose packaging capacity is disabled;

(b) culturing the cell obtained in step (a) under conditions that allow expression of said modified EBV genome;
(c) inducing the replicative phase of EBV; and
(d) isolating said particle,
wherein said modified EBV genome further comprises at least one difference in comparison to a wildtype EBV genome lacking one or more sequences encoding EBV polypeptides that are required for B-cell transformation and/or comprising one or more sequences encoding EBV polypeptides whose B-cell transformation capacity is disabled and wherein the polypeptide whose transformation capacity is disabled is the LMP-1 polypeptide.

4. The method of claim 3, wherein said modified EBV genome further comprises at least one difference in comparison to a wildtype EBV genome lacking one or more sequences encoding EBV polypeptides that are required for inducing replication of an EBV and/or comprising one or more sequences encoding EBV polypeptides whose capacity for inducing EBV replication is disabled.

5. The method of claim 3 comprising after step (b) and prior to step (c) a further step (b') comprising: providing one or more viral or non-viral polypeptides, one or more viral or non-viral nucleic acid sequences and/or one or more vaccine adjuvants to said cell, wherein said one or more viral polypeptides or said one or more viral nucleic acid sequences are not EBV polypeptides or EBV nucleic acid sequences, respectively.

6. The method of claim 4, wherein the one or more EBV polypeptides that are required for inducing replication of an EBV which are lacking or said one or more EBV polypeptides whose capacity for inducing EBV replication is disabled are selected from the group consisting of BZLF1, BRLF1, BMLF1 and any combination thereof and wherein in step (c) of claim 3 the replicative phase is induced by providing to said cell the selected polypeptide(s).

7. The method of claim 6, wherein the selected polypeptide is BZLF1.

8. The method of claim 6, wherein said provision of said one or more EBV polypeptides or said BZLF1 to said cell is effected by expression of said one or more EBV polypeptides or said BZLF1 from a stably transfected vector in said cell.

9. The method of claim 8 wherein the expression of said one or more EBV polypeptides or said BZLF1 is inducibly regulated.

* * * * *